(12) United States Patent
Vallier et al.

(10) Patent No.: US 9,284,576 B2
(45) Date of Patent: Mar. 15, 2016

(54) IN VITRO HEPATIC DIFFERENTIATION

(75) Inventors: Ludovic Vallier, Cambridge (GB);
Sheikh Tamir Rashid, Cambridge (GB);
Nicholas Hannan, Cambridge (GB);
Hsin-Hua Cho, Cambridge (GB)

(73) Assignee: Cambride Enterprise Limited, Cambride (GB)

( * ) Notice: Subject to any disclaimer, the term of this patent is extended or adjusted under 35 U.S.C. 154(b) by 0 days.

(21) Appl. No.: 13/818,515

(22) PCT Filed: Aug. 25, 2011

(86) PCT No.: PCT/GB2011/001275
§ 371 (c)(1),
(2), (4) Date: Feb. 22, 2013

(87) PCT Pub. No.: WO2112/025725
PCT Pub. Date: Mar. 1, 2012

(65) Prior Publication Data
US 2013/0156743 A1 Jun. 20, 2013

(30) Foreign Application Priority Data
Aug. 25, 2010 (GB) ................................. 1014169.5

(51) Int. Cl.
*C12N 5/02* (2006.01)
*C12N 15/85* (2006.01)
*C12N 5/071* (2010.01)

(52) U.S. Cl.
CPC ............... *C12N 15/85* (2013.01); *C12N 5/067* (2013.01); *C12N 2501/115* (2013.01); *C12N 2501/155* (2013.01); *C12N 2501/16* (2013.01)

(58) Field of Classification Search
None
See application file for complete search history.

(56) References Cited

FOREIGN PATENT DOCUMENTS

| WO | WO-2006/127768 A2 | 11/2006 |
|---|---|---|
| WO | WO-2007/050043 A2 | 5/2007 |
| WO | WO-2009/012428 A2 | 1/2009 |
| WO | WO 2009027654 A1 * | 3/2009 |
| WO | WO-2009/090882 A1 | 7/2009 |
| WO | WO 2010014949 A2 * | 2/2010 |
| WO | WO 2010/049752 A1 | 5/2010 |
| WO | WO 2010049752 A1 * | 5/2010 |

OTHER PUBLICATIONS

Song et al, Cell Research, 2009, 19:1233-1242.*
Wu et al. "Stem cell gene therapy: the risks of insertional mutagenesis and approaches to minimize genotoxicity." Front. Med. 2011, 5(4): pp. 356-371.*
Maier et al. "Retroviral vectors for gene therapy." Future Microbiol.(2010);5(10): pp. 1507-1523.*
Yee et al. "Turning Somatic Cells into Pluripotent Stem Cells." Nature Education (2010); 3(9): pp. 1-5.*
Saha et al. "Technical challenges in using human induced pluripotent stemcells to model disease." Cell Stem Cell. (Dec. 2009 ); 5(6): pp. 584-595.*
O'Neil. "Can iPS Cells Reprogram Disease Modeling?" Drug, Discovery and Development Magazine,e—Published Oct. 20, 2010.*
Rosselló et al. "Mammalian genes induce partially reprogrammed pluripotent stem cells in non-mammalian vertebrate and invertebrate species." Elife. (Sep. 2013); 2:pp. 1-24.*
Valdimarsdottir et al. "Functions of the TGFbeta superfamily in human embryonic stem cells." APMIS. (2005);113(11-12):pp. 773-789.*
D'Amour et al. "Efficient differentiation of human embryonic stem cells to definitive endoderm." Nature Biotechnology(2005); 23: pp. 1534-1541.*
Touboul et al. "Generation of Functional Hepatocytes from Human Embryonic Stem Cells Under Chemically Defined Conditions that Recapitulate Liver Development." Hepatology (May 2010); 51( 5): pp. 1754-1765.*
Park et al. "Disease-specific induced pluripotent stem (iPS) cells." Cell. (Sep. 2008;134(5):pp. 877-886.*
Hershfield "Adenosine Deaminase Deficiency." (Oct. 2006) Gene Review.*
International Search Report and Written Opinion for PCT/GB2011/001275, dated Dec. 28, 2011, 14 pages.
Gai et al., "Generation of Murine Hepatic Lineage Cells from Induced Pluripotent Stem Cells", Differentiation, 79(2): 171-181 (2010).
James et al., TGFb/activin/nodal Signaling is Necessary for the Maintenance of Pluripotency in Human Embryonic Stem Cells, Development, Company of Biologists, 132: 1273-1282 (2005).
McLean et al., Activin a Efficiently Specifies Definitive Endoderm from Human Embryonic Stem Cells only when Phosphatidylinositol 3-kinase Signaling is Suppressed, Stem Cells, 25(10): 29-38 (2007).

(Continued)

*Primary Examiner* — Thaian N Ton
*Assistant Examiner* — Titilayo Moloye
(74) *Attorney, Agent, or Firm* — Choate Hall & Stewart LLP; Charles E. Lyon, JD; Robert N. Sahr, JD

(57) ABSTRACT

This invention relates to the induction of hepatic differentiation by culturing induced pluripotent stem (iPS) cells in an endoderm induction medium to produce a population of anterior definitive endoderm (ADE) cells and then culturing the population of ADE cells in a hepatic induction medium to produce a population of hepatic progenitor cells, which may be optionally differentiated into hepatocytes. The endoderm induction medium is a chemically defined medium which has fibroblast growth factor activity, stimulates SMAD2 and SMAD3 mediated signalling pathways and SMAD1, SMAD5 and SMAD9 mediated signalling pathways, and inhibits phosphatidylinositol 3-kinase (PI3K) and glycogen synthase kinase 3β (GSK3β); and the hepatic induction medium is a chemically defined medium which stimulates SMAD2 and SMAD3 mediated signalling pathways. These methods may be useful, for example, in producing hepatocytes and hepatic progenitor cells for cell-based therapies or disease modelling.

12 Claims, 19 Drawing Sheets

(56) References Cited

OTHER PUBLICATIONS

Song et al., Efficient Generation of Hepatocyte-like Cells from Human Induced Pluripotent Stem Cells, Cell Research, 19(11): 1233-1242 (2009).

Touboul et al., Generation of Functional Hepatocytes from Human Embryonic Stem Cells Under Chemically Defined Conditions that Recapitulate Liver Development, Hepatology, 51(5): 1754-1762 (2010).

Vallier et al., Signaling Pathways Controlling Pluripotency and Early Cell Fate Decisions of Human Induced Pluripotent Stem Cells, Stem Cells, 27(11): 2655-2666 (2009).

Vallier et al., Early Cell Fate Decisions of Human Embryonic Stem Cells and Mouse Epiblast Stem Cells are controlled by the Same Signalling Pathways, Plos One, 4(6); 1-13 (2009).

Si-Tayeb, K. et al., Highly Efficient Generation of Human Hepatocyte-Like Cells from Induced Pluripotent Stem Cells, Hepatology, 51(1): 297-305 (2010).

\* cited by examiner

IN VITRO HEPATIC DIFFERENTIATION

This invention relates to the in vitro induction of hepatic differentiation in pluripotent human cells, in particular human iPS cells.

The possibility of deriving human induced pluripotent stem cells (hIPSCs) by over-expressing just a few transcription factors in somatic cells has opened new opportunities for regenerative medicine and in vitro disease modelling [1]. hIPSCs have since been generated from patients suffering from various diseases [2][3][4] with several groups reporting disease specific phenotypes when these cells were subsequently differentiated to neural progenitors [5][6]. To date, however, no hIPSC-based models have been reported for diseases specific to non-neuronal cells (such as cells of mesoderm and endoderm lineages), nor of diseases that arise as a consequence of loss of functions that are only seen in fully differentiated adult cells (late onset diseases). Furthermore, concerns remain that the cellular stresses inherent in reprogramming and differentiation prevent hIPSC derived cell models from preserving the myriad of subtle interactions governing the trafficking and activity of proteins. Understanding these interactions is central to understanding various disease mechanisms and may also provide insights into currently unexplained variations in clinical phenotypes observed between individuals of identical genetic backgrounds [7][8] [9].

These issues are particularly pertinent to liver disease and in particular inherited metabolic disorders of the liver (IMDs). This group of diseases result from genetic mutations that affect key proteins within hepatocytes. Whilst they may be treated by whole organ liver transplant, this procedure carries considerable risk. There is therefore a need for greater understanding of the disease mechanisms and development of alternative therapies [10] [11]. Such investigations are hampered by the difficulty in culturing primary hepatocytes and an inability to provide relevant human hepatocyte-like cell lines that faithfully replicate the protein dysfunction and subsequent cellular defects responsible for the disease [12].

This invention relates to a process for the high efficiency in vitro induction of human iPS cells into hepatic progenitor cells and hepatocytes. This may be useful, for example, in producing hepatocytes for cell-based therapies or disease modelling.

An aspect of the invention provides a method for inducing hepatic differentiation comprising;
  (i) providing a population of induced pluripotent stem (iPS) cells,
  (ii) culturing the population in a endoderm induction medium to produce a population of anterior definitive endoderm (ADE) cells,
    wherein the endoderm induction medium is a chemically defined medium which has fibroblast growth factor activity and which stimulates SMAD2 and SMAD3 mediated signalling pathways and SMAD1, SMAD5 and SMAD9 mediated signalling pathways and inhibits phosphatidylinositol 3-kinase (PI3K) and glycogen synthase kinase 3β (GSK3β); and,
  (iii) culturing the population of ADE cells in a hepatic induction medium to produce a population of hepatic progenitor cells,
    wherein the hepatic induction medium is a chemically defined medium which stimulates SMAD2 and SMAD3 mediated signalling pathways.

The method may further comprise;
  (iv) culturing the population of hepatic progenitor cells in a hepatic maturation medium to produce a population of hepatocytes.

Preferably the iPS cells are human iPS cells.

iPS cells are pluripotent cells which are derived from non-pluripotent, fully differentiated ancestor cells. Suitable ancestor cells include adult fibroblasts and peripheral blood cells. Ancestor cells are typically reprogrammed by the introduction of pluripotency genes or proteins, such as Oct4, Sox2 and Sox1 into the cell. The genes or proteins may be introduced into the differentiated cells by any suitable technique, including plasmid or more preferably, viral transfection or direct protein delivery. Other genes, for example Kif genes, such as Kif-1, -2, -4 and -5; Myc genes such as C-myc, L-myc and N-myc; nanog; and Lin28 may also be introduced into the cell to increase induction efficiency. Following introduction of the pluripotency genes or proteins, the ancestor cells may be cultured. Cells expressing pluripotency markers may be isolated and/or purified to produce a population of iPS cells. Techniques for the production of iPS cells are well-known in the art (Yamanaka et al Nature 2007; 448:313-7; Yamanaka 6 2007 Jun. 7; 1(1):39-49. Kim et al Nature. 2008 Jul. 31; 454(7204):646-50; Takahashi Cell. 2007 Nov. 30; 131(5): 861-72. Park et al Nature. 2008 Jan. 10; 451(7175):141-6; Kim et al Cell Stem Cell. 2009 Jun. 5; 4(6):472-6; Vallier, L., et al. Stem Cells, 2009. 9999(999A): p. N/A.).

An iPS cell may express one or more of the following pluripotency associated markers: Oct4, Sox2, alkaline phosphatase, SSEA-3, Nanog, SSEA-4, Tra-l-60, KLF-4 and c-myc.

In some embodiments, iPS cells used in the methods described herein are derived from healthy cells, such as fibroblasts, obtained from an individual, i.e. cells without a disease-associated phenotype or genotype. iPS cells derived from healthy cells may be used as described herein to produce hepatocytes which display a normal (i.e. non-disease associated) phenotype.

Healthy cells may be obtained from an individual with normal liver function or a patient with damaged or dysfunctional liver cells, for example a patient with liver damage or disease, such as hepatitis (e.g. hepatitis A, B, C, D, E, G or K), cirrhosis, hepatocellular carcinoma, non alcoholic fatty liver disease, drug induced liver injury, alcoholic liver disease or autoimmune liver disease.

In some embodiments, iPS cells may be derived from healthy cells obtained from individuals with distinct genetic backgrounds. For example, iPS cells may be produced from healthy cells from individuals having a liver disease, individuals having a high risk of a liver disease and/or individuals with a low risk of liver disease. Hepatocytes produced as described herein from individuals with distinct genetic backgrounds may be useful in studying the mechanisms of liver disease and identifying therapeutic targets.

Hepatocytes which display a normal (i.e. non-disease associated) phenotype may be useful in treating patients with liver damage or disease, as described below, for example, a patient who was the source of the healthy cells from which the iPS cells were derived.

In other embodiments, iPS cells used in the methods described herein are derived from disease-associated cells obtained from an individual i.e. cells which display a phenotype or genotype associated with a liver disease or dysfunction, for example an inherited metabolic disease (IMD) of the liver, such as alpha 1 antitrypsin deficiency, glycogen storage disease, for example glycogen storage disease type 1a, familial hypercholesterolemia, hereditary tyrosinaemia, Crigler Najjar syndrome, ornithtine transcarbamylase deficiency, or factor IX deficiency or other haemophilia, haemochromatosis, Wilson's disease, Dubin-Johnson syndrome, familial amyloidosis, or Refsum's disease. Any cell with the genotype, for example a genetic mutation or defect, which is associated with the IMD or other liver disease, may be employed, although samples of fibroblasts, e.g. dermal fibroblasts, may be conveniently obtained.

iPS cells derived from disease-associated cells obtained from an individual (i.e. disease specific iPS cells: ds-IPS or dhIPS) may be used as described herein to produce hepatocytes which display a liver disease associated phenotype, for example an IMD phenotype. Typically, the hepatocytes will contain the genetic mutation or defect which is associated with the liver disease. These cells may be useful in treating patients with liver damage or disease as described above or in liver disease modelling and screening.

In other embodiments, iPS cells derived from disease-associated cells obtained from an individual with a liver disease (i.e. disease specific iPS cells: ds-IPS or dhIPS) contain a genetic mutation or defect which is associated with the liver disease, such as Glu342Lys in α1-antitrypsin, which is responsible for A1AT deficiency. The mutation or defect may be corrected in the iPS cells before differentiation. For example, a nucleotide sequence in the ds-IPS cells which contains a disease associated genetic mutation or lesion may be replaced with the wild-type nucleotide sequence. Suitable methods for the correction of genetic mutations and defects are well-known in the art and described elsewhere herein. These corrected iPS cells (c-IPSCs) may be useful in treating patients with liver damage or disease as described above.

Liver diseases are described above, and may include inherited metabolic disorders (IMDs). An IMD may be an IMD associated with protein misfolding in the ER, such as α1-antitrypsin deficiency; a liver related receptoropathy, such as familial hypercholesterolaemia (FH); a metabolic disorder, for example a glycogen storage disease, such as GSD1a.

The liver disease may be a late-onset disorder or a disorder associated with mature adult liver cells.

Following production, a population of iPS cells may be cultured or maintained using conventional techniques (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)). For example, iPS cells, in particular human iPS cells, suitable for use in the present methods may be conventionally cultured in a culture dish on a layer of feeder cells, such as irradiated mouse embryonic fibroblasts (MEF), e.g. in Knockout (KS) medium supplemented with 4 ng/ml FGF2, at an appropriate density (e.g. $10^5$ to $10^6$ cells/60 mm dish), or on an appropriate substrate with feeder conditioned or defined medium.

Preferably, early passage iPS cells are used in the methods described herein. Early passage iPS cells are cells which have been cultured through 40 passages or less, preferably 35 passages or less, or 30 passages or less. iPS cells for use in the present methods may be passaged by enzymatic or mechanical means.

Suitable culture media for iPS cells include Knockout (KS) medium supplemented with 4 ng/ml FGF2; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human FGF2; and DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin.

Preferably, cells are harvested during culture using collagenase-free reagents, for example Accutase™ (BioWest).

The differentiation of iPS cells into hepatocytes according to the methods described herein occurs in three stages. In the first stage, the population of iPS cells differentiates into a population of anterior definitive endoderm (ADE) cells. In the second stage, the ADE cells differentiate into hepatic progenitors and in an optional third stage, the hepatic progenitors differentiate into hepatocytes. All the media used in these methods are chemically defined and are preferably humanised.

To induce differentiation into ADE cells, the population of iPS cells is cultured in an endoderm induction medium.

The endoderm induction medium is a chemically defined medium (CDM) which (i) stimulates signalling pathways mediated by SMAD1, SMAD2, SMAD3, and SMAD5; (ii) inhibits phosphatidylinositol 3-kinase (PI3K) and glycogen synthase kinase 3β (GSK3β); and (iii) has fibroblast growth factor (FGF) activity.

A chemically defined medium is a nutritive solution for culturing cells which contains only specified components, preferably components of known chemical structure. Preferably, the chemically defined medium is humanised. A humanised chemically defined medium is devoid of components or supplements derived from non-human animals, such as Foetal Bovine Serum (FBS), Bovine Serum Albumin (BSA), and mouse feeder cells.

The endoderm induction medium comprises a chemically defined basal medium.

Suitable chemically defined basal media include IMDM and/or F12 supplemented with insulin, for example at 0.5 μg/ml to 70 μg/ml, transferrin, for example at a concentration of 1.5 μg/ml to 150 μg/ml, an antioxidant, such as 1-thiolglycerol, for example at a concentration of 45 μM to 4.5 mM, and lipids.

Suitable chemically defined basal media include Johansson and Wiles C D M (Johansson and Wiles (1995) Mol Cell Biol 15, 141-151) which is supplemented with polyvinyl alcohol, insulin, transferrin and defined lipids. Johansson and Wiles C D M consists of: 50% IMDM (Gibco) plus 50% F12 NUT-MIX (Gibco); 7 μg/ml insulin; 15 μg/ml transferrin; 1 mg/ml polyvinyl alcohol (PVA; 1% chemically defined lipid concentrate (Invitrogen); and 450 μM 1-thiolglycerol.

Other suitable chemically defined basal medium are known in the art. In order to avoid the use of Bovine or Human serum albumin, the chemically defined basal medium is supplemented in the endoderm induction medium with polyvinyl alcohol (PVA) at a concentration of 0.5 mg/ml to 50 mg/ml. Chemically defined basal medium supplemented with polyvinyl alcohol is commonly referred to as CDM-PVA.

In the endoderm induction medium, the CDM-PVA is supplemented with additional factors, preferably recombinant human factors, which induce the iPS cells to differentiate into anterior definitive endoderm (ADE) cells.

For example, the CDM-PVA is supplemented with fibroblast growth factor. Fibroblast growth factor is a protein factor which stimulates cellular growth, proliferation and cellular differentiation by binding to a fibroblast growth factor receptor (FGFR). Suitable fibroblast growth factors include any member of the FGF family, for example any one of FGF1 to FGF14 and FGF15 to FGF23.

Preferably, the fibroblast growth factor is FGF2 (NCBI GeneID: 2247, nucleic acid sequence NM_002006.3 GI: 41352694, amino acid sequence NP_001997.4 GI: 41352695); FGF7 (also known as keratinocyte growth factor (or KGF), NCBI GeneID: 2247, nucleic acid sequence NM_002006.3 GI: 41352694, amino acid sequence NP_001997.4 GI: 41352695); or FGF10 (NCBI GeneID: 2247, nucleic acid sequence NM_002006.3 GI: 41352694, amino acid sequence NP_001997.4 GI: 41352695).

Most preferably, the fibroblast growth factor is FGF2 (Amit, M., et al. *Developmental Biology* 227:271-278 (2000)).

Fibroblast growth factors, such as FGF2, FGF7 and FGF10, may be produced using routine recombinant techniques or obtained from commercial suppliers (e.g. R&D Systems, Minneapolis, Minn.; Stemgent Inc, USA).

Conveniently, the concentration of FGF in the endoderm induction medium may be from 1 to 500 ng/ml, preferably about 40 ng/ml.

The CDM-PVA may be further supplemented with a first TGFβ ligand which stimulates SMAD2 and SMAD3 mediated intracellular signalling pathways in the iPS cells.

TGFβ ligands are peptides of the TGFβ superfamily. Members of the TGFβ superfamily possess a characteristic structure and are well-known in the art.

The first TGFβ ligand may be Activin or TGFβ.

Activin (Activin A: NCBI GeneID: 3624 nucleic acid reference sequence NM_002192.2 GI: 62953137, amino acid reference sequence NP_002183.1 GI: 4504699) is a dimeric polypeptide which exerts a range of cellular effects via stimulation of the Activin/Nodal pathway (Vallier et al., *Cell Science* 118:4495-4509 (2005)). Activin is readily available from commercial sources (e.g. Stemgent Inc. MA USA). Conveniently, the concentration of Activin in the medium may be from 10 to 1000 ng/ml, preferably about 100 ng/ml.

TGFβ (NCBI GeneID: 7040 nucleic acid reference sequence NM_000660.4 GI: 260655621, amino acid reference sequence NP_000651.3 GI: 63025222) is a homodimeric polypeptide which regulates proliferation and differentiation (Watabe, T. et al (2009). Cell Res. 19:103-115). Recombinant human TGFβ is readily available from commercial sources (e.g. Stemgent Inc. MA USA). Conveniently, the concentration of TGFβ in the medium may be from 10 to 1000 ng/ml, preferably about 100 ng/ml.

The CDM-PVA may be further supplemented with a second TGFβ ligand which stimulates SMAD1, SMAD5 and SMAD9 mediated intracellular signalling pathways in the iPS cells.

The second TGFβ ligand may be a Bone Morphogenic Protein (BMP). Bone Morphogenic Proteins bind to Bone Morphogenic Protein Receptors (BMPRs) and stimulate intracellular signalling through pathways mediated by SMAD1, SMAD5 and SMAD9. Suitable Bone Morphogenic Proteins include any member of the BMP family, for example BMP2, BMP3, BMP4, BMP5, BMP6 or BMP7. Preferably the second TGFβ ligand is BMP2 (NCBI GeneID: 650, nucleic acid sequence NM_001200.2 GI: 80861484; amino acid sequence NP_001191.1 GI: 4557369) or BMP4 (NCBI GeneID: 652, nucleic acid sequence NM_001202.3 GI: 157276592; amino acid sequence NP_001193.2 GI: 157276593).

Bone Morphogenic Proteins may be produced using routine recombinant techniques or obtained from commercial suppliers (e.g. R&D, Minneapolis, USA, Stemgent Inc, USA).

Conveniently, the concentration of a Bone Morphogenic Protein, such as BMP2 or BMP4 in the medium may be from 1 to 500 ng/ml, preferably about 10 ng/ml The endoderm induction medium may thus comprise a chemically defined basal medium supplemented with poly-vinyl alcohol, FGF, first and second TGFβ ligands, a PI3K inhibitor and a GSK3β inhibitor.

PI3K inhibitors inhibit the activity of phosphatidylinositol 3-kinases, such as phosphatidylinositol-4,5-bisphosphate 3-kinase (EC2.7.1.153).

Suitable PI3K inhibitors include wortmannin; LY301497 (17-b-hydroxywortmannin); LY294002 (2-morpholin-4-yl-8-phenylchromen-4-one: Maclean et al (2007) *Stem Cells* 25 29-38); CLB1309 (KN309: (±)-2({1-[7-methyl-2-(morpholin-4-yl)-4-oxo-pyrido[1,2-a]pyrimidin-9-yl]ethyl}amino) benzoic acid); PX-866 ((1E,4S,4aR,5R,6aS,9aR)-5(Acetyloxy)-1-[(di-2-propen-1-ylamino)methylene]-4,4a,5,6,6a,8, 9,9a-octahydro-11-hydroxy-4-(methoxymethyl)-4a,6a-dimethylcyclopenta[5,6]naphtho[1,2-c]pyran-2,7,10(1H)-trione); IC87114 (quinolone pyrrolopyrimidine; #6 FIG. 17); GDC-0941 (#3 FIG. 17; 2-(1H-Indazol-4-yl)-6-[[4-(methylsulfonyl)-1-piperazinyl]methyl]-4-(4-morpholinyl)-thieno [3,2-d]pyrimidine); TGX-221 (7-methyl-2-(4-morpholinyl)-9-[1-(phenylamino)ethyl]-4H-pyrido[1,2-a]pyrimidin-4-one), quercetin; BEZ235 (#4 FIG. 17); XL147 (#1 FIG. 17); X1765 (#2 FIG. 17); PX-866 (#5 FIG. 17); ZSTK474 (2-(2-difluoromethylbenzimidazol-1-yl)4,6-dimorpholino-1,3,5-triazine); and SF1126 (2-[2-methoxyethylamino]-8-phenyl-4H-1-benzopyran-4-one). Other PI3K inhibitors are available in the art.

Suitable PI3K inhibitors may be obtained from commercial suppliers (e.g. Calbiochem CA USA).

For example, the endoderm induction medium may contain 1 to 100 µM PI3K inhibitor, such as LY294002, preferably about 10 µM.

GSK3β inhibitors inhibit the activity of glycogen synthase kinase 3β (Gene ID 2932: EC2.7.11.26). Suitable inhibitors include CHIR99021 (6-((2-((4-(2,4-Dichlorophenyl)-5-(4-methyl-1H-imidazol-2-yl)pyrimidin-2-yl)amino)ethyl) amino)nicotinonitrile; Ring D. B. et al., Diabetes, 52:588-595 (2003)) alsterpaullone, kenpaullone, SB216763 (3-(2,4-dichlorophenyl)-4-(1-methyl-1H-indol-3-yl)-1H-pyrrole-2, 5-dione), and SB415286 (3-[(3-chloro-4-hydroxyphenyl) amino]-4-(2-nitrophenyl)-1H-pyrrole-2,5-dione).

Suitable glycogen synthase kinase 3β inhibitors may be obtained from commercial suppliers (e.g. Stemgent Inc. MA USA; Cayman Chemical Co. MI USA). For example, the endoderm induction medium may contain 0.3 to 30 µM of a GSK3β inhibitor, such as CHIR99021, preferably about 3 µM.

In some embodiments, the endoderm induction medium may consist of CDM-PVA basal medium supplemented with Activin, FGF2, BMP-4, a phosphatidylinositol 3-kinase inhibitor, preferably LY294002, and a glycogen synthase kinase 3β inhibitor, preferably CHIR99021.

Preferably, Activin, FGF2 and BMP-4 in the endoderm induction medium are all recombinant human proteins.

The culture of mammalian cells is well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho WY et al J Immunol Methods. (2006) 310:40-52, Handbook of Stem Cells (ed. R. Lanza) ISBN: 0124366430). Media and ingredients thereof may be obtained from commercial sources (e.g. Gibco, Roche, Sigma, Europa bioproducts, R&D Systems). Standard mammalian cell culture conditions may be employed, for example 37° C., 21% Oxygen, 5% Carbon Dioxide. Media is preferably changed every two days and cells allowed to settle by gravity.

Preferably the cells are cultured in a monolayer, in the absence of feeder cells, on a substrate coated with serum, preferably human serum or extracellular matrix protein, such as fibronectin, laminin or collagen. Suitable culture techniques are well known in the art.

In preferred embodiments, the differentiation of iPS cells into anterior definitive endoderm (ADE) cells may be performed in three separate steps. For example, differentiation of the population of iPS cells into ADE cells may comprise;

(a) culturing the population of iPSCs in endoderm induction medium, for example for 12 to 36 hours, preferably about 24 hours, (b) further culturing the population in endoderm induction medium without the glycogen synthase kinase 3β inhibitor, for example for 12 to 36 hours, preferably about 24 hours, and, (c) further culturing the population in an ADE induction medium which stimulates SMAD2 and SMAD3 signalling pathways and which has fibroblast growth factor activity, for example for 12 to 36 hours, preferably about 24 hours, to produce the population of anterior definitive endoderm (ADE) cells.

The ADE induction medium is a chemically defined medium which comprises a chemically defined basal medium. Suitable chemically defined basal media include RPMI-1640.

RPMI-1640 (Moore, G. E. and Woods L. K., (1976) Tissue Culture Association Manual. 3, 503-508) is a serum-free basal medium containing inorganic salts, amino acids, vitamins, antioxidants and buffers. RPMI-1640 is well known in the art and readily available from commercial sources (e.g. Sigma-Aldrich MI USA). The components of RPMI-1640 medium are shown in Table 2.

The chemically defined basal medium may be supplemented with a serum-free media supplement. Suitable serum-free media supplements include B27 (Brewer et al J. Neurosci Res 35 567-576 (1993)) and NS21 (Chen et al J. Neurosci Meths (2008) 171 239-247). Serum-free media supplements, such as B27 and N21, are well known in the art and widely available commercially (e.g. Invitrogen; Sigma Aldrich Inc).

In the ADE induction medium, the chemically defined basal medium is also supplemented with additional factors, preferably recombinant human factors, to produce the population of anterior definitive endoderm (ADE) cells. For example, the chemically defined basal medium may be supplemented with fibroblast growth factor (FGF) and a first TGFβ ligand which stimulates SMAD2 and SMAD3 mediated intracellular signalling pathways. FGF and first TGFβ ligands are described in more detail above.

In some embodiments, the ADE induction medium may comprise a chemically defined basal medium supplemented with 1 to 1000 ng/ml first TGFβ ligand, such as activin, preferably 100 ng/ml, and 4 to 400 ng/ml FGF, such as FGF2, preferably 40 ng/ml FGF. The chemically defined basal medium may be RPMI-1640 supplemented with B27 or NS21 media supplements.

Preferably, the population of iPS cells is cultured for 2 to 4 days, most preferably 3 days to produce the population of ADE cells.

Anterior definitive endoderm (ADE) cells may express endoderm markers, such as Sox17, foxA2, GSC, Mixl1, Lhx1, CXCR4, GATA6, Eomes and Hex.

Anterior definitive endoderm (ADE) cells may lack expression of pluripotency markers or markers associated with ectodermal or mesodermal lineages. For example the ADE cells may not express at detectable levels one or more, preferably all, of the following; Oct4, Sox2, alkaline phosphatase, SSEA-3, Nanog, SSEA-4, Tra-1-60 and KLF-4.

The expression of one or more ADE cell markers and/or one or more pluripotent cell markers may be monitored and/or detected in the population of differentiating cells. This allows the extent of differentiation or endoderm induction of the cell population to be determined.

After differentiation, the population of ADE cells may be substantially free from other cell types. For example, the population may contain 85% or more, 90% or more, 95% or more, or 98% or more ADE cells, following culture in the medium. Preferably, the population of ADE cells is sufficiently free of other cell types that no purification is required. If required, the population of ADE cells may be purified by any convenient technique, such as FACS.

In some embodiments, the population of ADE cells may be expanded before further differentiation into a hepatic lineage. ADE cells may be expanded by any convenient technique, for example in an FGF supplemented medium, such as ADE induction medium, as described above.

To induce differentiation into hepatic progenitor cells, the population of ADE cells is cultured in a hepatic induction medium. The hepatic induction medium is a chemically defined medium (CDM) which stimulates signalling pathways mediated by SMAD2 and SMAD3 and induces differentiation into a hepatic lineage.

The hepatic induction medium comprises a chemically defined basal medium supplemented with one or more additional factors, preferably recombinant human factors, which induce the ADE cells to differentiate into hepatic progenitor cells.

Suitable chemically defined basal media (CDM) include RPMI-1640, which is described above. The CDM may be supplemented with a first TGFβ ligand which stimulates SMAD2 and SMAD3 mediated signalling pathways, such as TGFβ or activin, as described above. Preferably, the medium is supplemented with 5 to 500 ng/ml of a first TGFβ ligand, such as activin, preferably about 50 ng/ml.

The population of ADE cells may be cultured for 4 to 6 days, preferably about 5 days, to produce the population of hepatic progenitor cells.

The expression of one or more hepatic progenitor cell markers and/or one or more ADE cell markers may be monitored and/or detected in the population of differentiating cells. This allows the extent of differentiation to be determined as it is cultured.

Hepatic progenitor cells are capable of differentiating into either hepatocytes or into cholangiocytes and express markers of both lineages. Hepatic progenitor cells may express one or more of alpha-fetoprotein (AFP), cytokeratin 18 (CK18), cytokeratin 19 (CK19), hepatocyte nuclear factor 4 (HNF4), and hepatocyte nuclear factor 6 (HNF6). The detection of one or more of these markers is indicative of differentiation into a hepatic lineage.

The population of hepatic progenitor cells may be substantially free from other cell types. For example, the population may contain 80% or more, 85% or more, 90% or more, or 95% or more hepatic progenitor cells, following culture in the medium.

Preferably, the population of hepatic progenitor cells is sufficiently free of other cell types that no purification is required. If required, the population of hepatic progenitor cells may be purified by any convenient technique.

Following culturing in the medium as described above, the population of hepatic progenitor cells may be isolated and/or removed from the medium. Suitable techniques are well-known in the art.

Hepatic progenitor cells may be expanded, maintained in culture, stored, for example frozen using conventional techniques, or used in therapeutic or other applications as described herein.

For example, hepatic progenitor cells may be used in cell-based therapies, as described below.

In some embodiments, a method may comprise inducing the hepatic progenitor cells to differentiate into hepatocytes. To induce differentiation, the population of hepatic progenitor cells is cultured in a hepatic maturation medium which consists of a chemically defined basal medium (CDM) supplemented with additional factors, preferably recombinant human factors, to induce the hepatic progenitor cells to mature into hepatic progenitor cells.

Suitable chemically defined basal media (CDM) include CMRL and hepatozyme SFM. (GIBCO™; Invitrogen Inc).

CMRL basal medium is a serum-free basal medium which is well known in the art and readily available from commercial sources (e.g. Cat No: 11530037 Invitrogen; Product #C0422 Sigma). The composition of CMRL medium is shown in Table 3.

Hepatozyme SFM is a serum-free basal medium which is available from commercial sources (e.g. Cat No 17705; Invitrogen).

The chemically defined medium (CDM) medium may be supplemented with one or more factors which induce differentiation and maturation of hepatoblasts or hepatic progenitor into hepatocytes. For example, the basal medium may be supplemented with hepatocyte growth factor (HGF) or epidermal growth factor (EGF).

Hepatocyte growth factor (HGF) (NCBI GeneID: 3082, nucleic acid sequence NM_000601.4 GI: 58533168, amino acid sequence NP_000592.3 GI: 33859835) is a mesenchymally derived mitogen which is a member of the plasminogen subfamily of S1 peptidases. HGF may be produced using routine recombinant techniques or obtained from commercial suppliers (e.g. Peprotech Inc NJ USA). Conveniently, the concentration of HGF in the medium may be from 2 to 200 µg/ml, preferably about 20 µg/ml.

Epidermal Growth Factor (EGF) (NCBI GeneID: 1950, nucleic acid sequence NM_001178130.1 GI: 296011012 amino acid sequence NP_001171601.1 GI: 296011013; Reynolds, B. A. et al. J. Neurosci. 12: 4565-4574 (1992)) is a growth factor which regulates proliferation and differentiation through binding to its receptor (EGFR). EGF may be produced using routine recombinant techniques or obtained from commercial suppliers (e.g. Peprotech Inc NJ USA, Stemgent Inc USA). Conveniently, the concentration of EGF in the medium may be from 2 to 200 µg/ml, preferably about 20 µg/ml The chemically defined medium (CDM) medium may also be supplemented with one or more factors which induce differentiation and maturation of hepatocyte, such as oncostatin-M. Oncostatin-M (NCBI GeneID: 5008, nucleic acid sequence NM_020530.3 GI: 28178862, amino acid sequence NP_065391.1 GI: 10092621) is a cytokine of the IL-6 family. Oncostatin-M may be produced using routine recombinant techniques or obtained from commercial suppliers (e.g. R&D Systems, MN USA; Abcam Ltd, UK). Conveniently, the concentration of Oncostatin-M in the medium may be from 1 to 100 µg/ml, preferably about 10 µg/ml.

The population of hepatic progenitor cells may be cultured for 10 to 40, preferably about 25 days to produce the population of hepatocytes.

Hepatocytes may express one or more of albumin, $\alpha 1$-antitrypsin (AAT), a cytochrome p450 (CYP), such as CYP3A4, CYP1A2, CYP2E1, CYP2C19, CYP2C9, and CYP2D6, factor IX, apopoliprotein A2, CEBP$\alpha$ and transthyretin.

In some embodiments, hepatocytes may not express one or more progenitor markers, such as AFP, CK18 and Sox17.

The expression of one or more hepatic progenitor markers and/or one or more hepatocyte markers may be monitored and/or detected in the population of cells. For example, the expression or production of albumin and/or $\alpha 1$-antitrypsin by the population of hepatocytes may be determined. This allows the extent of differentiation in the population of cultured to be determined and/or monitored. The expression of cell markers may be determined by any suitable technique, including immunocytochemistry, immunofluorescence, RT-PCR, fluorescence activated cell sorting (FACS), and enzymatic analysis.

The ability of cells in the population to perform one or more hepatocyte functions may be monitored and/or determined. For example, the ability of the cells to perform one or more of detoxification, glycogen storage, secretion of AAT or albumin, bile production, thrombopoietin production, angiotensinogen production, conversion of ammonia to urea (urea cycle), cholesterol synthesis, glycogenolysis, glycogenesis and lipogenesis may be monitored and/or determined.

The population of hepatocytes may be substantially free from other cell types. For example, the population may contain 80% or more, 85% or more, 90% or more, or 95% or more hepatocytes, following culture in the medium. The presence or proportion of hepatocytes in the population may be determined through the expression of albumin and/or $\alpha 1$-antitrypsin as described above.

Preferably, the population of hepatocytes is sufficiently free of other cell types that no purification is required. If required, the population of hepatocytes may be purified by any convenient technique, including FACS.

ADE cells, hepatic progenitors and/or hepatocytes produced at any stage in the methods described herein may be isolated and/or purified. Cells may be separated from other cell types in the population using any technique known to those skilled in the art, including those based on the recognition of extracellular epitopes by antibodies and magnetic beads or fluorescence activated cell sorting (FACS) including the use of antibodies against extracellular regions of characteristic markers as described below.

A population of hepatocytes produced as described herein may be expanded, cultured or maintained using standard mammalian cell culture techniques.

In some embodiments, the population of hepatocytes produced as described herein may be stored, for example by lyophilisation and/or cryopreservation.

The population of hepatocytes may be admixed with other reagents, such as buffers, carriers, diluents, preservatives or pharmaceutically acceptable excipients. Suitable reagents are described in more detail below.

As described above, disease specific iPS cells may be used to produce hepatocytes which display a phenotype associated with a liver disease, such as an IMD. A hepatocyte with a disease-associated phenotype may display one or more pathologies associated with the disease.

A method as described herein may comprise detecting or measuring one or more disease-pathologies in the population of hepatocytes.

Disease pathologies may include one or more of aberrant growth, increased apoptosis, aberrant gene expression; aberrant response to glucagon stimulation; protein aggregation or polymerisation; protein entrapment in the ER; cholesterol uptake; lipid and/or glycogen accumulation; lactic acid production; and deficiencies in one or more hepatocyte functions set out above, in said population of hepatocytes A method of producing hepatocytes with disease pathology may comprise;

inducing in vitro hepatic differentiation of a population of ds-iPS cells as described above, thereby producing a population of hepatocytes with disease pathology.

ds-iPS cell derived hepatocytes may display disease pathologies within 10, 20, 40 or days after the initiation of differentiation from the ds-iPS cell.

Once produced, hepatocytes with a disease phenotype, such as an IMD phenotype, may be cultured, expanded and maintained, for example for use in screening. A method of maintaining hepatocytes with a disease phenotype may comprise culturing a population of hepatocytes with a disease phenotype derived from ds-iPS cells, as described above.

Another aspect of the invention provides a population of isolated hepatocytes or a population of hepatic progenitor cells produced by a method described above.

The population may contain 80% or more, 85% or more, 90% or more, or 95% or more hepatocytes or hepatic progenitor cells.

Hepatocytes produced by the methods described herein may display one or more functions or functional characteristics specific to mature hepatocytes. For example, the hepatocytes may be able to store glycogen and LDL, secrete AAT and/or albumin, metabolize drugs via the CytP450 pathway and express GFP protein under the control of the hepatocyte specific ApoAII promoter. The hepatocytes may be able to produce one or more of bile, thrombopoietin, angiotensinogen, urea and cholesterol; and perform one or more of glycogenolysis, glycogenesis and lipogenesis.

In some embodiments, the hepatocytes may not be fully differentiated into mature adult hepatocytes and may continue to express one or more progenitor markers, such as AFP; express reduced levels of Alb and/or display reduced CYP3A4 activity compared to mature adult hepatocytes.

Hepatocytes may display one or more of the following characteristics: occasional binucleity; glycogen deposits; apical microprotrusions; rough and smooth endoplasmic reticulum (ER) and a prominent Golgi body.

Hepatocytes or hepatic progenitor cells produced by the methods described herein do not express the exogenous reprogramming factors used to produce the iPS cells, which may still be present in the cells as retroviral transgenes.

A population of hepatocytes or hepatic progenitor cells may be used in methods of treatment of the human or animal body, for example the treatment of patients with damaged or dysfunctional hepatic tissue. A population may also be used in the manufacture of a medicament for use in the treatment of damaged or dysfunctional hepatic tissue. An individual with damaged or dysfunctional hepatic tissue may have hepatitis (e.g. hepatitis A, B, C, D, E, G or K), cirrhosis, hepatocellular carcinoma, non alcoholic fatty liver disease, drug induced liver injury, alcoholic liver disease, autoimmune liver disease or an inherited metabolic disorder such as Alpha 1 Antitrypsin deficiency, a Glycogen Storage Disease, for example Glycogen Storage Disease Type 1a, Familial Hypercholesterolemia, Hereditary Tyrosinaemia, Crigler Najjar syndrome, ornithtine transcarbamylase deficiency, or factor IX deficiency or other haemophilia, haemochromatosis, Wilson's disease, Dubin-Johnson syndrome, familial amyloidosis, and Refsum's disease. For therapeutic applications, the hepatocytes are preferably clinical grade hepatocytes.

A method of treating a patient with a damaged or dysfunctional hepatic tissue may comprise;

administering a population of hepatocytes or hepatic progenitor cells produced as described above to an individual in need thereof.

The population of hepatocytes may be transplanted, infused or otherwise administered into the liver of the individual. Suitable techniques are well known in the art.

The population of hepatocytes may be produced from iPS cells derived from cells obtained from the individual. In some embodiments, disease associated mutations or genetic defects in the iPS cells may be corrected before differentiation into hepatocytes or hepatic progenitor cells, as described above.

Aspects of the invention also extend to a pharmaceutical composition, medicament, drug or other composition comprising hepatocytes or hepatic progenitor cells produced as described herein, a method comprising administration of such hepatocytes or hepatic progenitor cells to a patient, e.g. for treatment (which may include preventative treatment) of damaged or dysfunctional hepatic tissue, as described above, and a method of making a pharmaceutical composition comprising admixing such hepatocytes or hepatic progenitor cells with a pharmaceutically acceptable excipient, vehicle or carrier, and optionally one or more other ingredients.

Hepatocytes or hepatic progenitor cells which are administered to an individual may be genetically manipulated to produce a therapeutic molecule, for example a drug or growth factor (Behrstock S et al, Gene Ther 2006 March; 13(5):379-88, Klein S M et al, Hum Gene Ther 2005 April; 16(4):509-21)

The present invention provides a composition containing hepatocytes or hepatic progenitor cells produced in accordance with the invention, and one or more additional components. Pharmaceutical compositions according to the present invention, and for use in accordance with the present invention, may comprise, in addition to the hepatocytes, a pharmaceutically acceptable excipient, carrier, buffer, preservative, stabiliser, anti-oxidant or other material well known to those skilled in the art. Such materials should be non-toxic and should not interfere with the activity of the hepatocytes. The precise nature of the carrier or other material will depend on the route of administration.

Liquid pharmaceutical compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

Hepatocytes or hepatic progenitor cells may be implanted into a patient by any technique known in the art (e.g. Lindvall, O. (1998) Mov. Disord. 13, Suppl. 1:83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-

1555, Le Blanc et al, Lancet 2004 May 1; 363(9419):1439-41). In particular cell suspensions may be injected into the portal vein of a patient.

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

In some embodiments, the hepatocytes or hepatic progenitor cells in the population produced as described herein may display a normal phenotype. For example, cells may be obtained from an individual with hepatic damage or dysfunction and used to produce iPS cells. In some embodiments, the iPS cells may contain a mutation or genetic defect and this mutation or defect may be corrected using conventional recombinant techniques to produce iPS cells with a normal phenotype. Hepatocytes or hepatic progenitors with a normal phenotype may be produced from these iPS cells as described herein and implanted into the patient to repair or ameliorate the hepatic damage or dysfunction.

In other embodiments, the hepatocytes or hepatic progenitor cells in the population produced as described herein may display a disease phenotype. For example, cells may be obtained from an individual with hepatic damage or dysfunction and used to produce disease-specific iPS (ds-iPS) cells. Hepatocytes or hepatic progenitors with a disease phenotype may be produced from these iPS cells as described herein. These cells may then be treated to restore a normal phenotype. For example, the genetic mutation or defect which is responsible for the disease phenotype may be corrected in vitro. Various techniques are available to correct genetic mutations or defects in isolated mammalian cells. Once the defect or mutation is corrected and the normal phenotype restored, the hepatocytes or hepatic progenitors may be implanted into the patient to repair or ameliorate the hepatic damage or dysfunction.

A population of hepatocytes produced as described above may be useful in modelling the interaction of test compounds with hepatic cells, for example in toxicity screening, modelling liver disease and screening for compounds with potential therapeutic effects.

A method of screening a compound may comprise;
 contacting a population of hepatocytes produced by a method described above with a test compound, and;
 determining the effect of the test compound on said hepatocytes and/or the effect of said hepatocytes on the test compound.

The hepatocytes may display a normal or a disease phenotype.

The growth or viability of the hepatocytes may be determined in the presence relative to the absence of the test compound. A decrease in growth or viability is indicative that the compound has a hepatotoxic effect.

Gene expression may be determined in the presence relative to the absence of the test compound. For example, the expression of albumin, α1-antitrypsin (AAT), a cytochrome p450 enzyme, such as CYP3A4, CYP1A2, CYP2E1, CYP2C19, CYP2C9, and CYP2D6, factor IX, apopoliprotein A2, CEBPα and/or transthyretin, may be determined. A decrease in expression is indicative that the compound has a hepatotoxic effect. Gene expression may be determined at the nucleic acid level, for example by RT-PCR, or at the protein level, for example, by immunological techniques, such as ELISA, or by activity assays. Cytochrome p450 assays, for example, luminescent, fluorescent or chromogenic assays are well known in the art and available from commercial suppliers.

The metabolism, degradation, or breakdown of the test compound by the hepatocytes may be determined. In some embodiments, changes in the amount or concentration of test compound and/or a metabolite of said test compound may be determined or measured over time, either continuously or at one or more time points. For example, decreases in the amount or concentration of test compound and/or increases in the amount or concentration of a metabolite of said test compound may be determined or measured. In some embodiments, the rate of change in the amount or concentration of test compound and/or metabolite may be determined. Suitable techniques for measuring the amount of test compound or metabolite include mass spectrometry.

This may be useful in determining the in vivo half-life, toxicity, efficacy or other in vivo properties of the test compound.

One or more functions of the hepatocytes may be determined and/or measured in the presence relative to the absence of the test compound. For example, the ability of the hepatocytes to perform one or more of detoxification of organic compounds, glycogen storage, secretion of AAT or albumin, bile production, thrombopoietin production, angiotensinogen production, conversion of ammonia to urea, cholesterol synthesis, glycogenolysis, glycogenesis and lipogenesis, may be determined and/or measured.

A decrease in the ability of the hepatocytes to perform one or more of these functions in the presence relative to the absence of the test compound is indicative that the compound has a hepatotoxic effect.

A method of screening for a compound useful in the treatment of a liver disease may comprise;
 contacting a population of hepatocytes produced as described above which display an disease phenotype with a test compound, and;
 determining the effect of the test compound on said hepatocytes.

The hepatocytes may display a disease phenotype. The effect of the test compound on one or more disease pathologies in the hepatocytes may be determined. For example, the effect of the test compound on one or more of cell growth, gene expression, protein aggregation or polymerisation; protein entrapment in the ER; cholesterol uptake; lipid and/or glycogen accumulation; and lactic acid production may be determined.

Suitable techniques are well known in the art and include immunostaining, mass spectrometry, Western blots, and enzymatic assays.

A decrease or amelioration of one or more disease pathologies in the hepatocytes in the presence, relative to the absence of test compound may be indicative that the test compound may be useful in the treatment of a liver disease, for example an inherited metabolic disorder. Examples of inherited metabolic disorders are provided above.

Methods as described herein may comprise the step of identifying a test compound which reduces or ameliorates one or more disease pathologies, for example IMD pathologies, in the hepatocytes. Compounds which reduce disease pathologies may be useful in the development of therapeutics for the treatment of the liver disease.

In other embodiments, the hepatocytes may display a normal phenotype and may, for example, be derived from an individual with a high risk of or high susceptibility to liver disease, relative to the general population. The effect of the test compound on one or more of cell growth, or gene expression, for example expression of a cytochrome p450 (CYP), such as CYP3A4, CYP1A2, CYP2E1, CYP2C19, CYP2C9, and CYP2D6, may be determined. The effect of the test compound on one or more functions of the hepatocytes may be determined. For example, the ability of the hepatocytes to perform one or more of detoxification of organic compounds, glycogen storage, secretion of AAT or albumin, bile production, thrombopoietin production, angiotensinogen production, conversion of ammonia to urea, cholesterol synthesis, glycogenolysis, glycogenesis and lipogenesis, may be determined and/or measured in the presence relative to the absence of the test compound.

An increase in gene expression, growth and/or one or more functions in the presence relative to the absence of the test compound may be indicative that the compound may be useful in the treatment of a liver disease, such as hepatitis (e.g. hepatitis A, B, C, D, E, G or K), cirrhosis, hepatocellular carcinoma, non alcoholic fatty liver disease, drug induced liver injury, alcoholic liver disease or autoimmune liver disease.

Following identification of a compound which reduces or ameliorates one or more disease pathologies in the hepatocytes, the compound may be modified to optimise its pharmaceutical properties. This may be done using modelling techniques which are well-known in the art.

A test compound identified using one or more initial screens as having ability to reduce or ameliorate one or more disease pathologies, such as IMD pathologies, in the hepatocytes may be assessed further using one or more secondary screens.

A secondary screen may involve testing for a biological function or activity in vitro and/or in vivo, e.g. in an animal model. For example, the ability of a test compound to reduce or ameliorate one or more symptoms or pathologies associated with the liver disease in an animal model of the disease may be determined.

Following identification of a test compound which reduces or ameliorates one or more disease pathologies in the hepatocytes, the compound may be isolated and/or purified or alternatively it may be synthesised using conventional techniques of recombinant expression or chemical synthesis. Furthermore, it may be manufactured and/or used in preparation, i.e. manufacture or formulation, of a composition such as a medicament, pharmaceutical composition or drug. These may be administered to individuals for the treatment of a liver disease.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

FIG. 1 shows a flow diagram outlining the protocol used to differentiate the dhIPSC library into hepatocytes.

Figure 2:
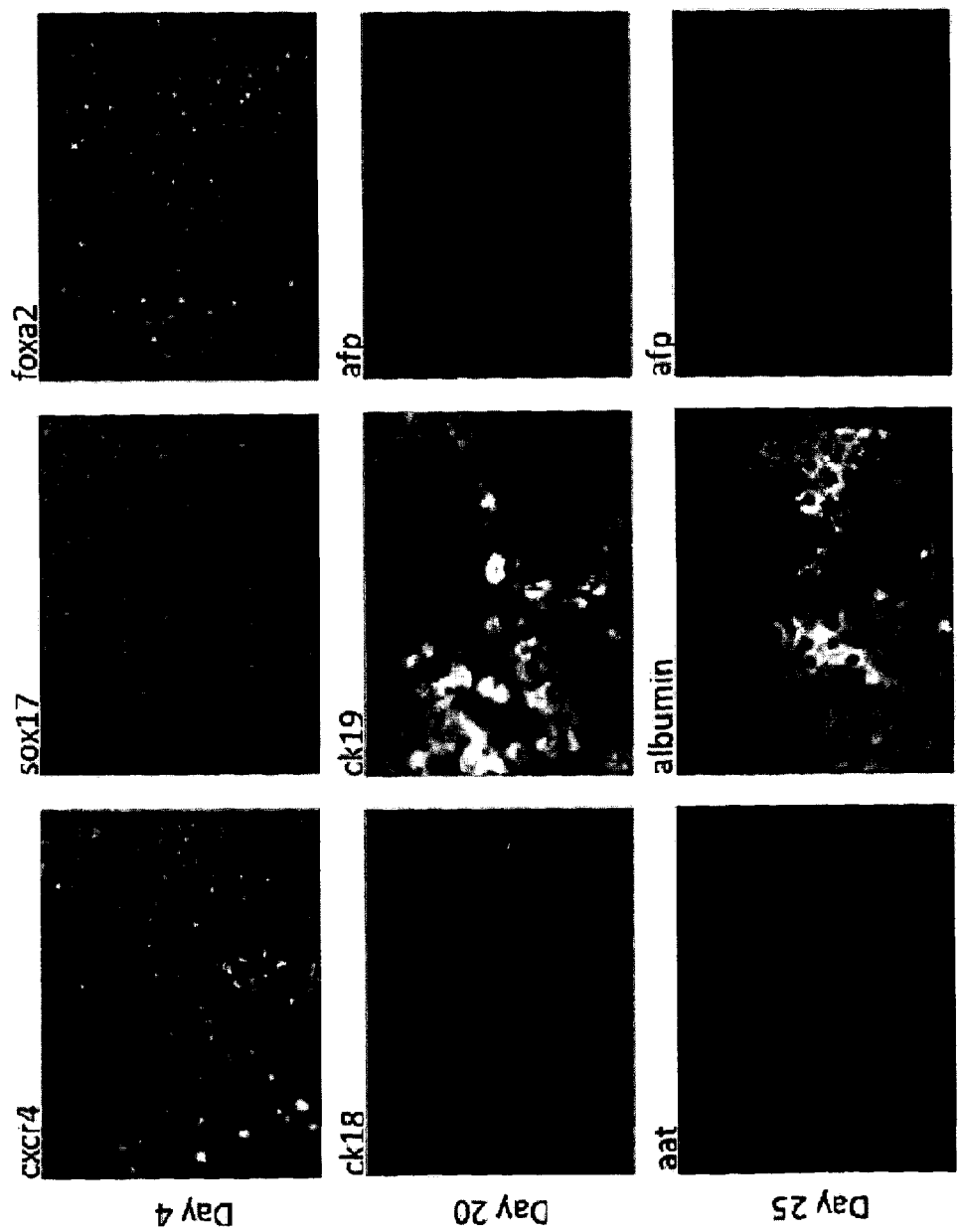

FIG. 2 shows immunostaining analyses for expression of specific proteins marking key stages of hepatocyte development (Day 4 Endoderm: CXCR4, Sox17 and Foxa2; Day 20 Hepatic progenitor CK18, CK19 and Alpha FetoProtein (AFP); Day 25 Foetal hepatocyte: Albumin (Alb), AFP and α1-antitrypsin (AAT).

Figure 3:
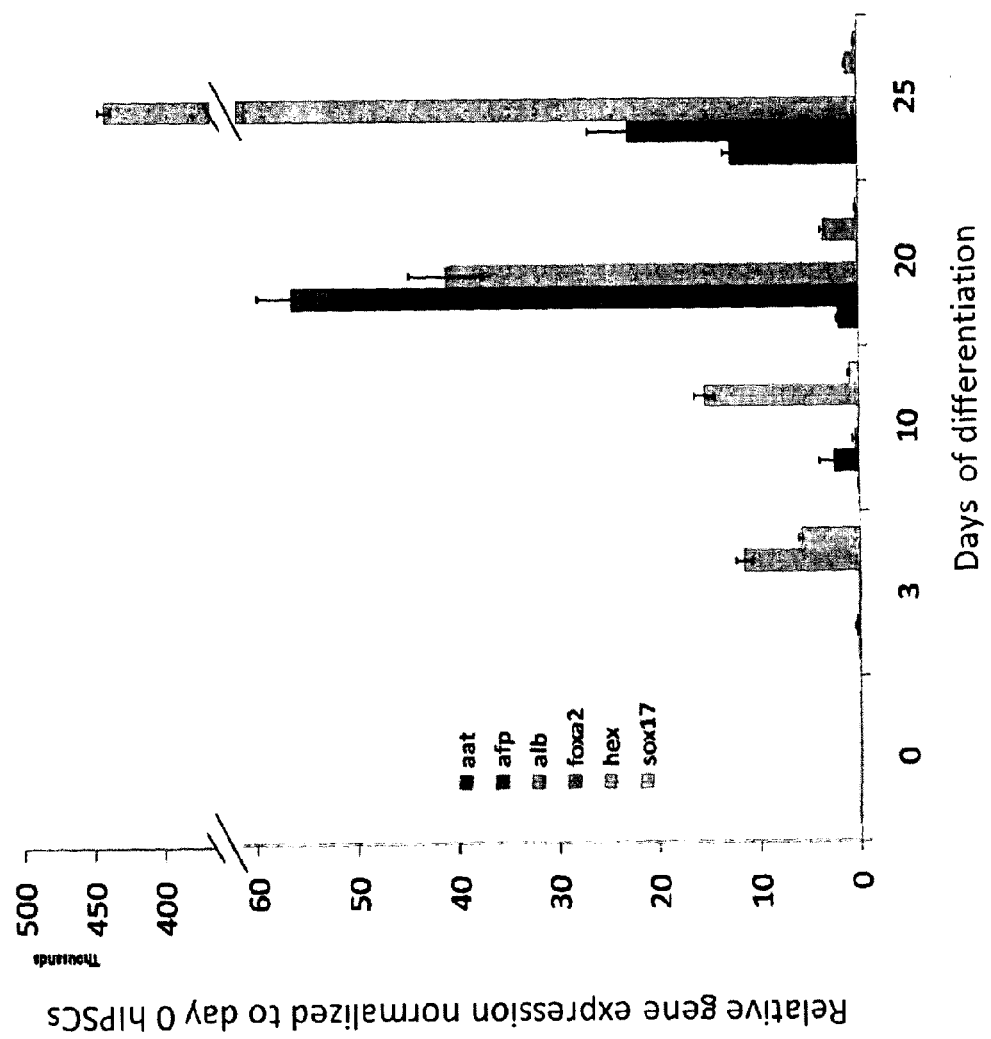

FIG. 3 shows real time PCR analysis for the expression of genes marking key stages of dhIPSCs differentiation to hepatocytes.

Figure 4:
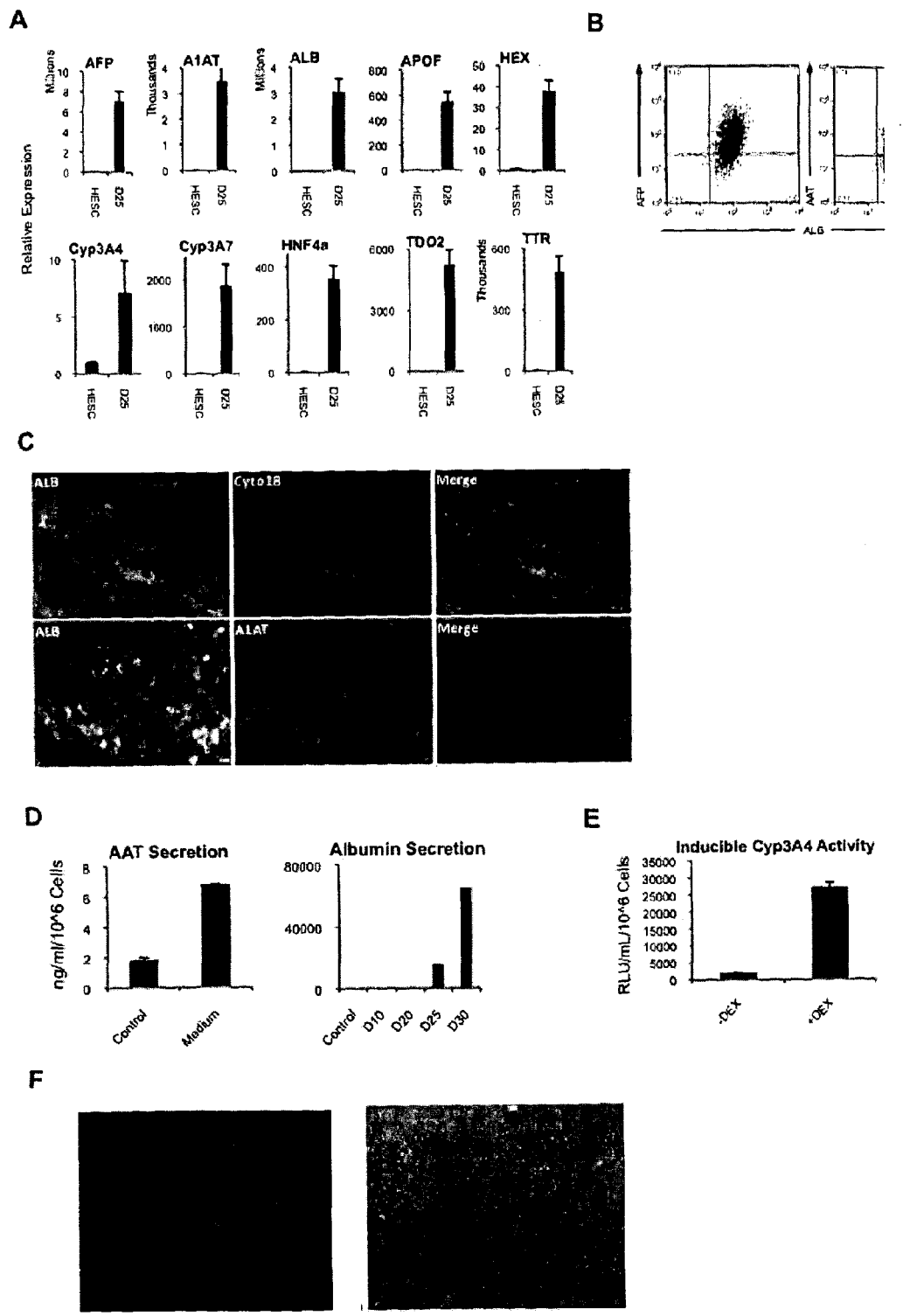

FIG. 4 shows the differentiation of hESCs derived definitive endoderm into foetal hepatocytes in defined culture conditions. FIG. 4A shows the expression of hepatocyte markers in DE cells grown for 25 days in conditions inductive for hepatic differentiation. FIG. 4B shows FACS analyses showing the co-expression of Albumin (ALB) α-1-antitrypsin (AAT) and α-1-Fetoprotein (AFP) in hESCs derived foetal hepatocytes (Day 25). FIG. 4C shows immunostaining analyses of the expression of Albumin (ALB), Cyokeratin 18 (CK18) and α-1-antitrypsin (AAT) in hESCs derived foetal hepatocytes (Day 25). Scale bar 50 µM. FIG. 4D shows ELISA analyses showing Alpha1-antytripsin (AAT) and Albumin secretion in culture media of hESCs derived foetal hepatocytes. FIG. 4E shows Inducible activity of CYP3A4 by dexamethasone (DEX) in hESCs derived foetal hepatocytes. FIG. 4F shows DIL assay showing up take of cholesterol and PAS staining showing glycogen storage in hESCs derived foetal hepatocytes. Scale bar 50 µM.

Figure 5:
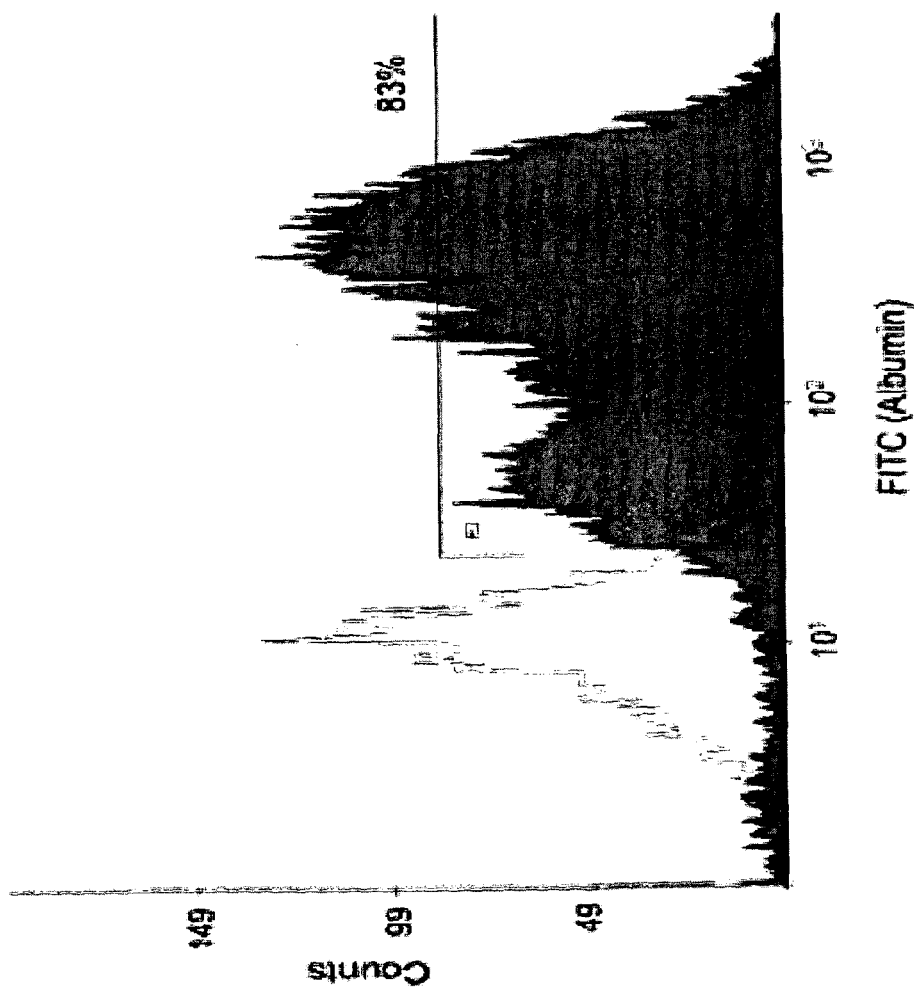

FIG. 5 shows the fraction of cells expressing albumin after 25 days of hepatic differentiation as shown by FACS analyses.

Figure 6:
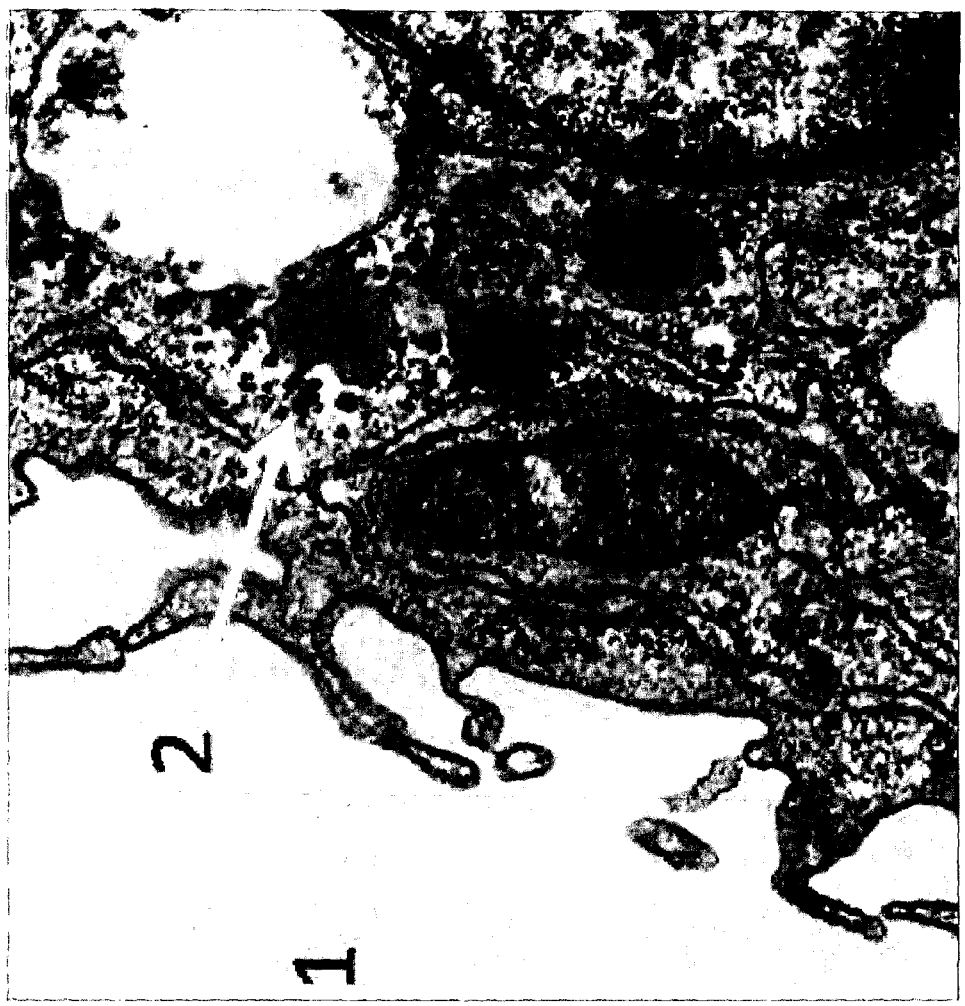

FIG. 6 shows morphologic analysis of dhIPSC derived hepatocytes (day 25) by transmission electron microscopy displaying presence of (1) apical microvilli and (2) glycogen rosettes. The data shown are taken from one line (patient 1; line 1) but are representative of all lines similarly characterized.

FIGS. 7 to 10 show the in vitro modelling of α1-antitrypsin deficiency (A1ATD) using dhIPSCs.

Figure 7:
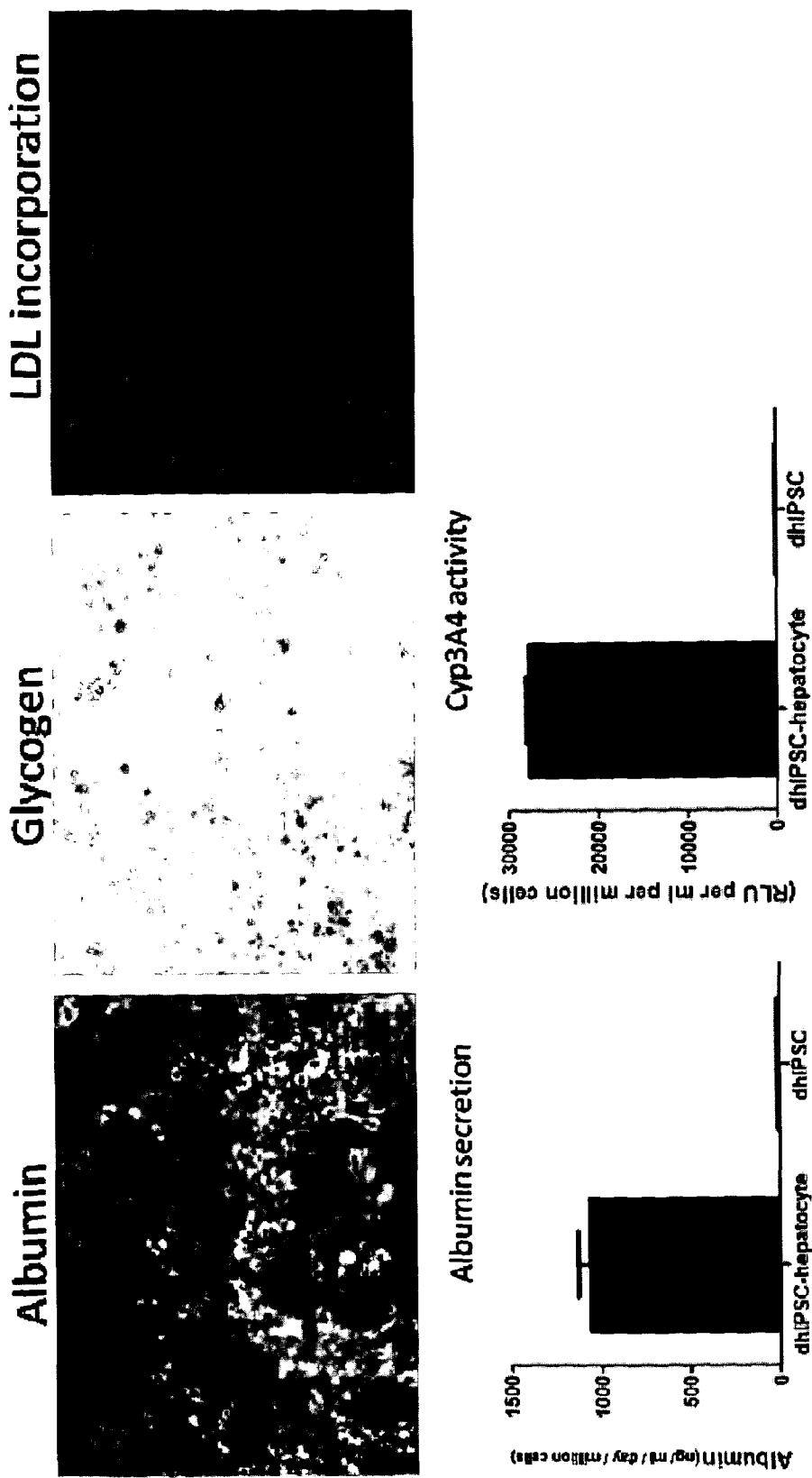

FIG. 7 shows 1ATD-dhIPSCs differentiated to hepatocytes display functional activity characteristic of primary human hepatocytes including the presence of intracellular albumin (Albumin), glycogen storage as shown by periodic acid Schiff staining (PAS) (Glycogen), Low Density Lipoprotein cholesterol uptake as shown by fluoresceinated Low Density Lipoprotein (DIL) incorporation (LDL incorporation), albumin secretion and active CytP450 metabolism (Cyp3A4 Activity).

Figure 8:
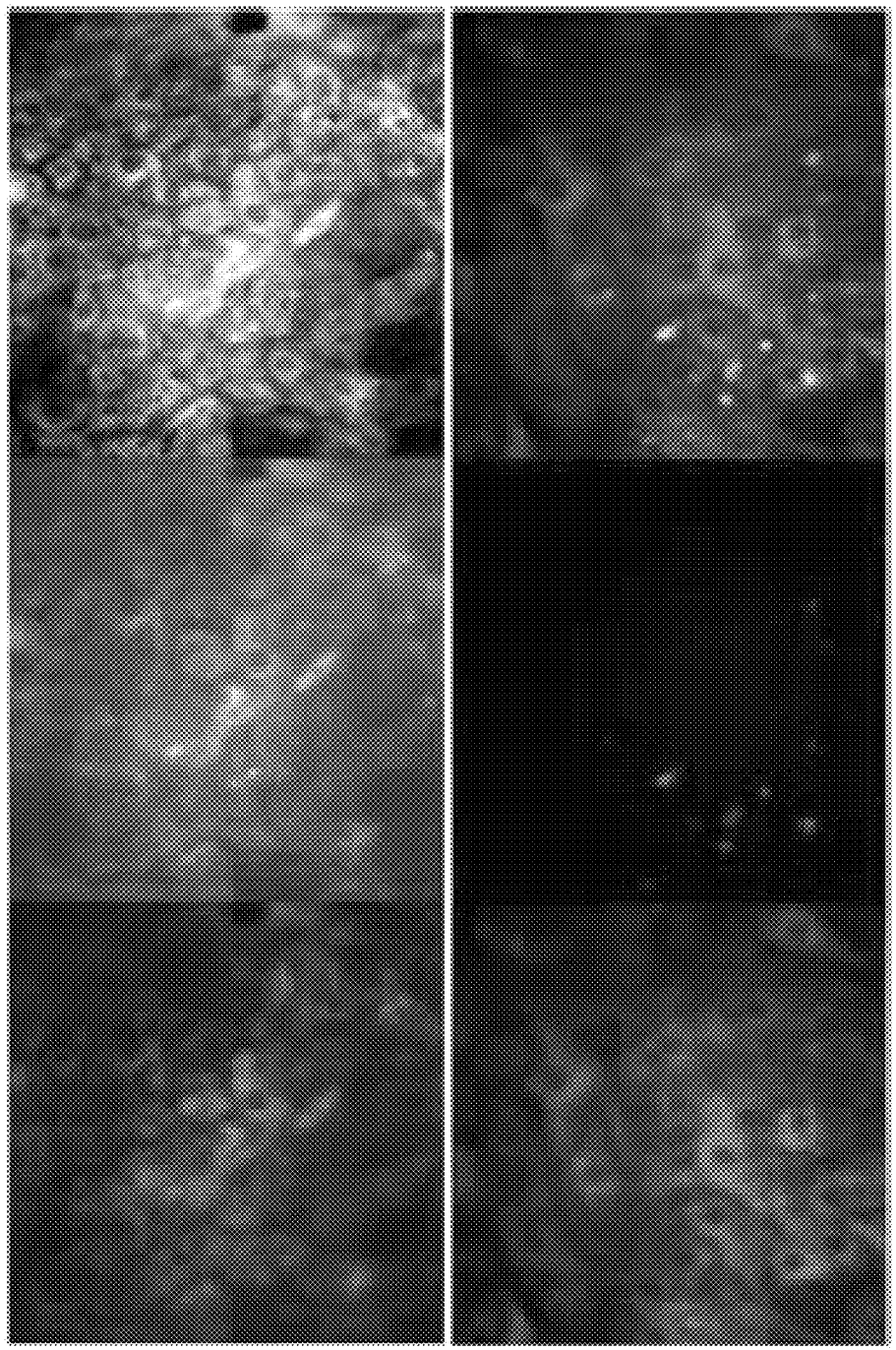

FIG. 8 shows immunostaining analyses for the expression of misfolded polymeric α1-antitrypsin using the polymer specific 2C1 antibody (middle panels, green fluorescence) or an antibody that detects all forms of α1-antitrypsin (left panels, red fluorescence) in patient specific (A1ATD, top row) and control hIPSC derived hepatocytes (control, bottom panels).

Figure 9:
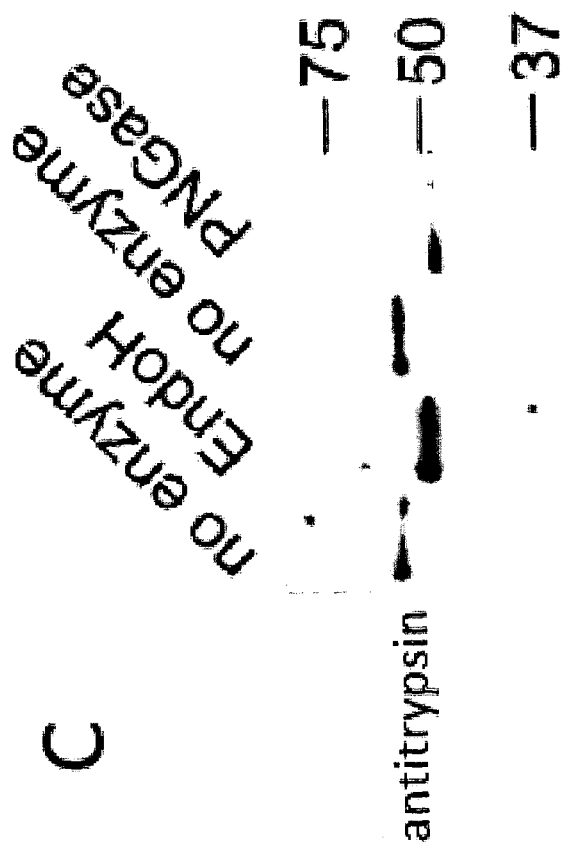

FIG. 9 shows endoglycosidase H (Endo H) digestion of A1ATD dhIPSC derived hepatocyte microsomal subcellular fraction confirming retention of misfolded polymeric α1-antitrypsin protein is within the endoplasmic reticulum. n=3

Figure 10:
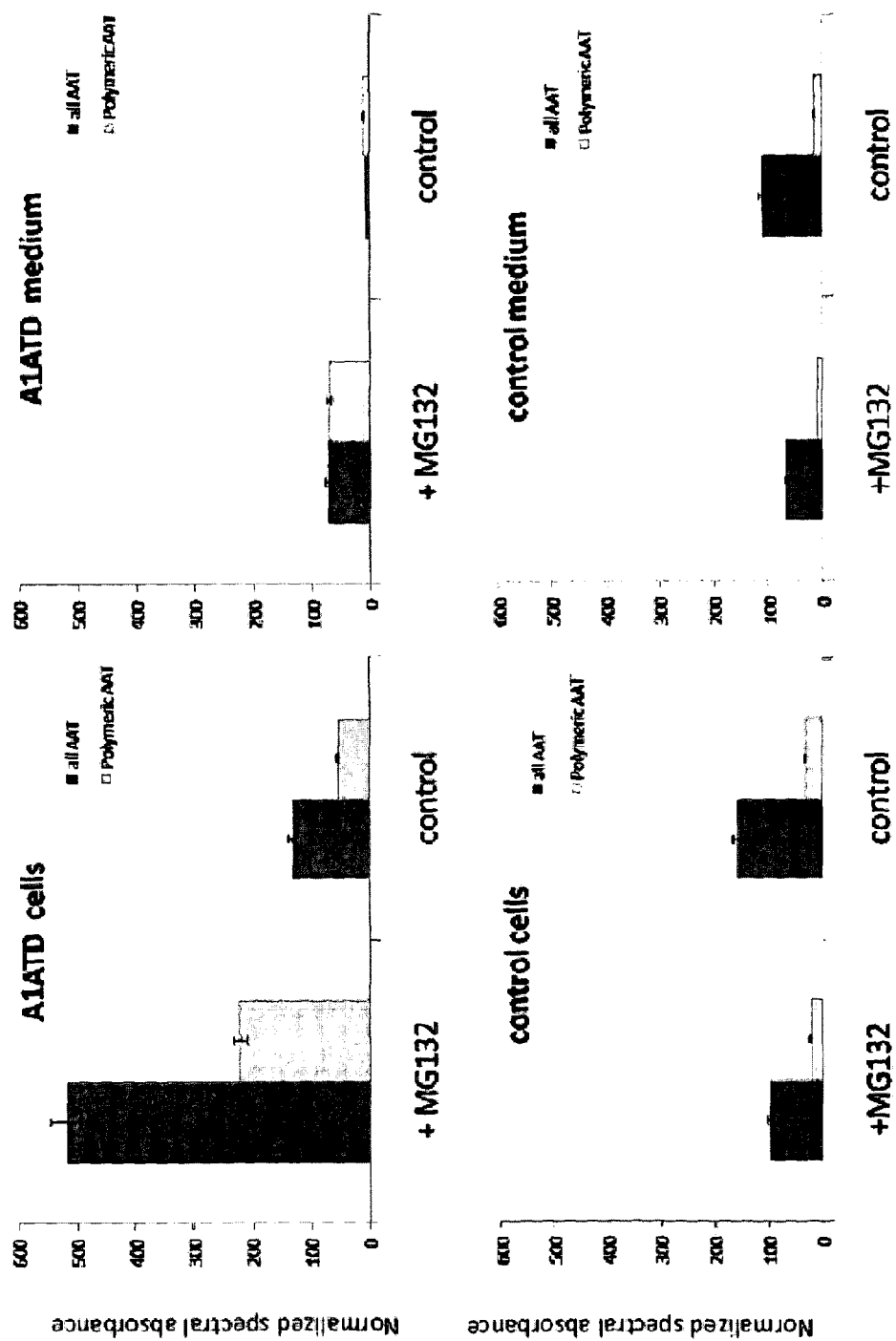

FIG. 10 shows ELISA to assess the intracellular expression (cells) and secretion (medium) of all (All) and polymeric (Polymeric) α1-antitrypsin protein in patient specific (A1ATD) and control hIPSC derived hepatocytes (control) following overnight proteosomal inhibition by MG132. n=3.

Figure 11:
Figure 11:
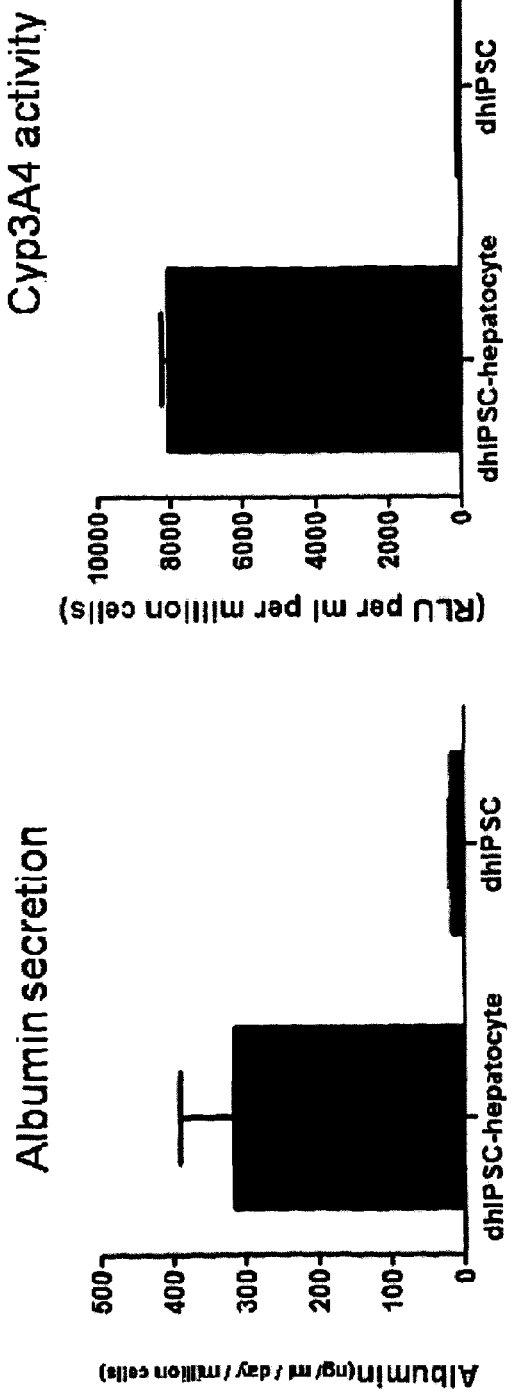
Figure 12:
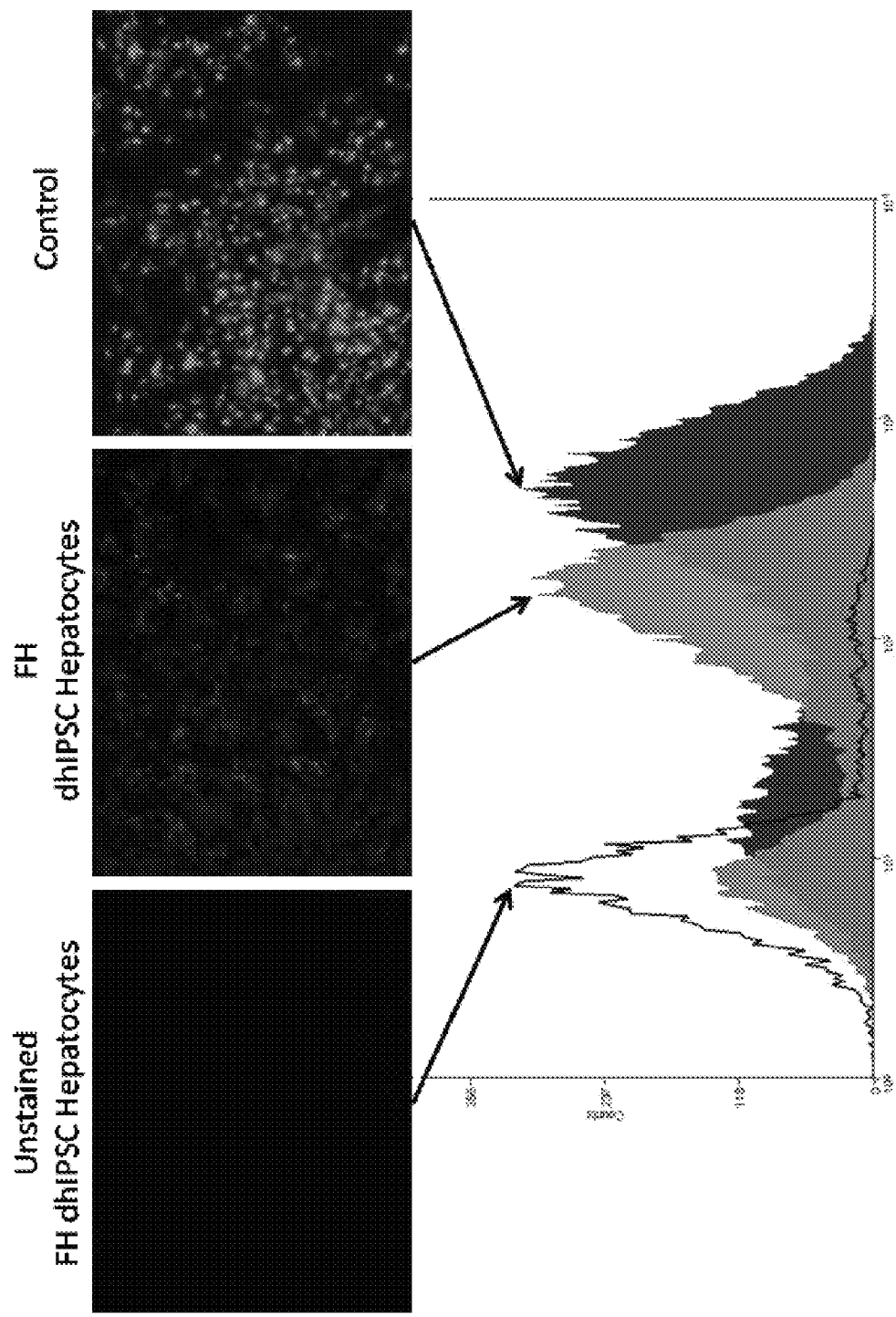

FIGS. 11 and 12 show in vitro modelling of familial hypercholesterolaemia using dhIPSCs.

FIG. 11 shows FH-dhIPSCs differentiated to hepatocytes display functional activity characteristic of primary human hepatocytes including intracellular presence of albumin (Albumin), glycogen storage (Glycogen), albumin secretion and active CytP450 metabolism (Cyp3A4 Activity)

FIG. 12 shows FACS analysis for fluoresceinated Low Density Lipoprotein incorporation confirmed FH-dhIPSC derived hepatocytes (FH, red curve) lack the ability to efficiently take up Low Density Lipoprotein compared to the positive control (Control, blue curve). hIPSCs grown in the absence of LDL were used as a negative control (unstained).

FIGS. 13 to 17 show in vitro modelling of Glycogen Storage Disease Type 1a using dhIPSCs.

Figure 13:
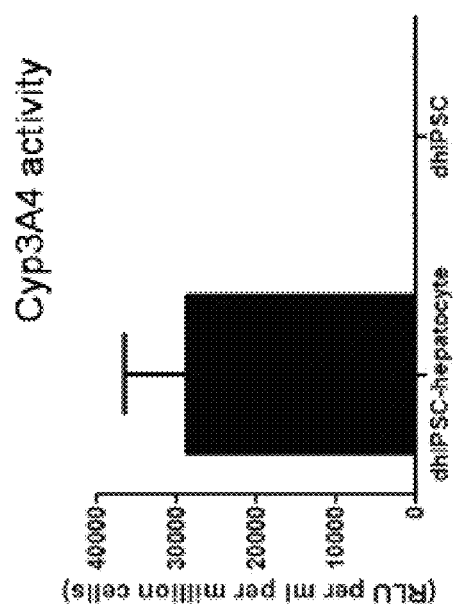
Figure 13:
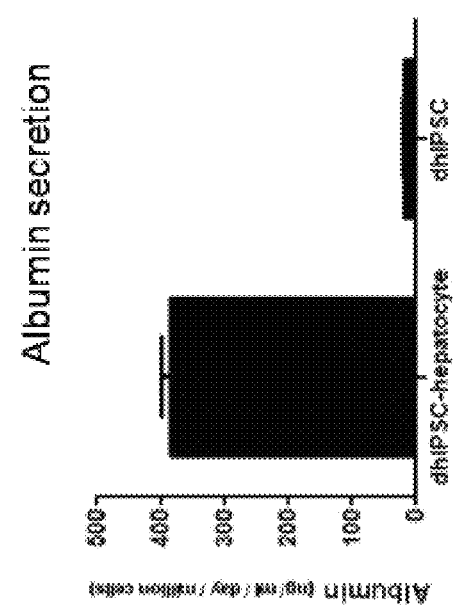
Figure 13:
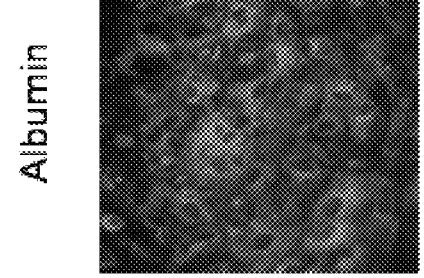

FIG. 13 shows GSD-dhIPSCs differentiated to hepatocytes display functional activity characteristic of primary human hepatocytes including intracellular presence of albumin (Albumin), Albumin secretion and active CytP450 metabolism (Cyp3A4 Activity).

Figure 14:
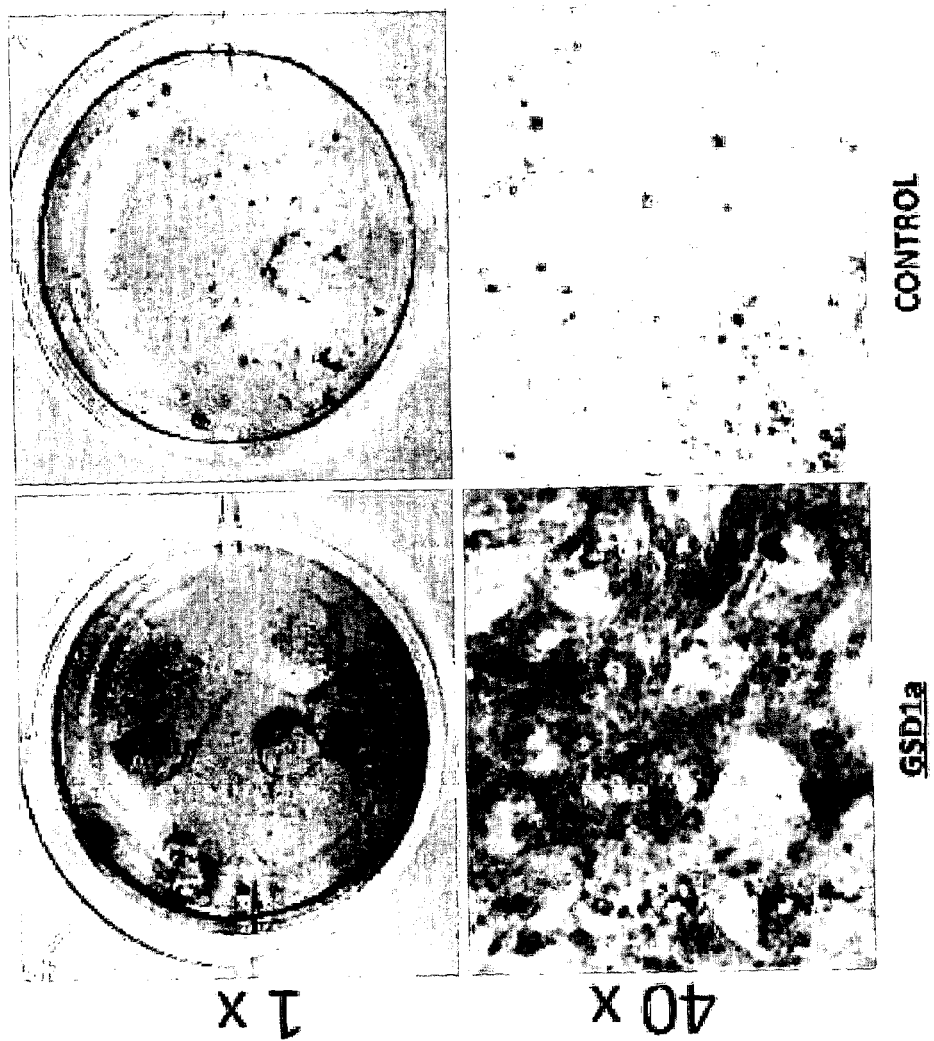

FIG. 14 shows periodic acid Schiff staining showing excessive accumulation of intracellular glycogen in GSD-dhIPSCs derived hepatocytes (GSD1a) compared to hIPSC derived hepatocytes from control subjects (Control). n=3

Figure 15:
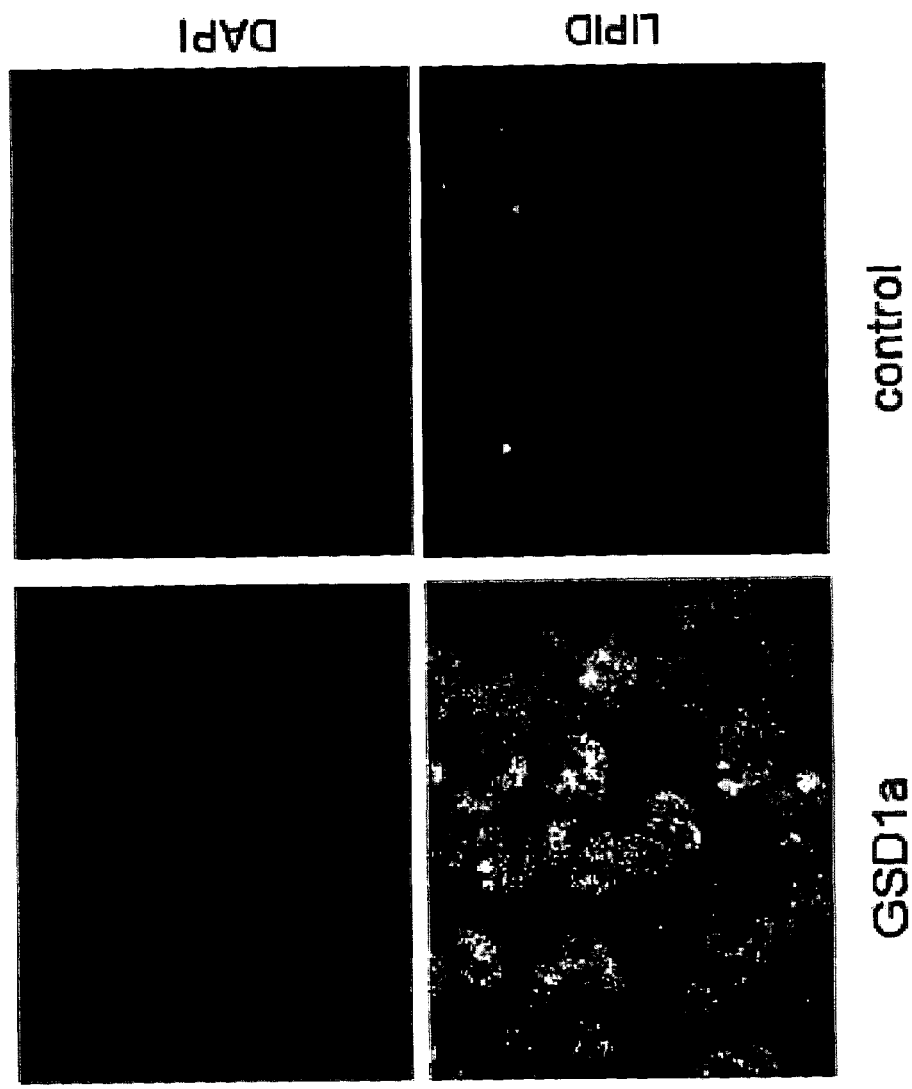

FIG. 15 shows BODIPY staining showing excessive accumulation of intracellular lipid in GSD-dhIPSC derived hepatocytes (GSD1a) compared to hIPSC derived hepatocytes from control subjects (Control). n=3

Figure 16:
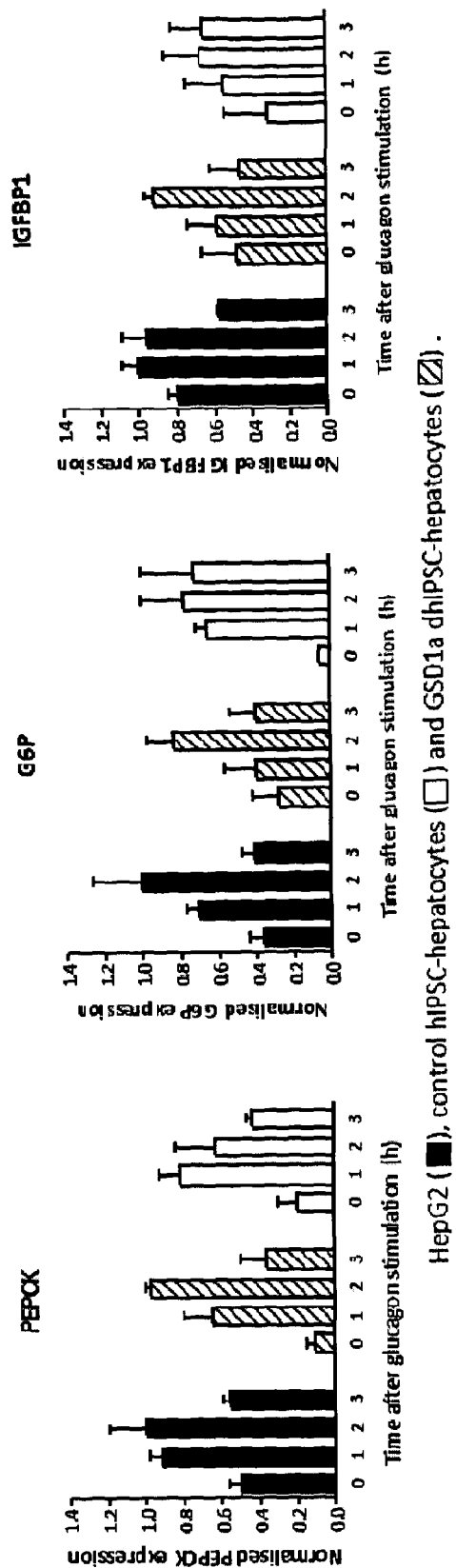

FIG. 16 shows dhIPSC derived hepatocytes appropriately upregulate transcriptional targets of glucagon as shown by qRT-PCR analysis of the expression of PEPCK, G6P and IGFBP1 analyzed 0, 1, 2 and 3 hours after stimulation with 100 nM glucagon hydrochloride. n=3

Figure 17:
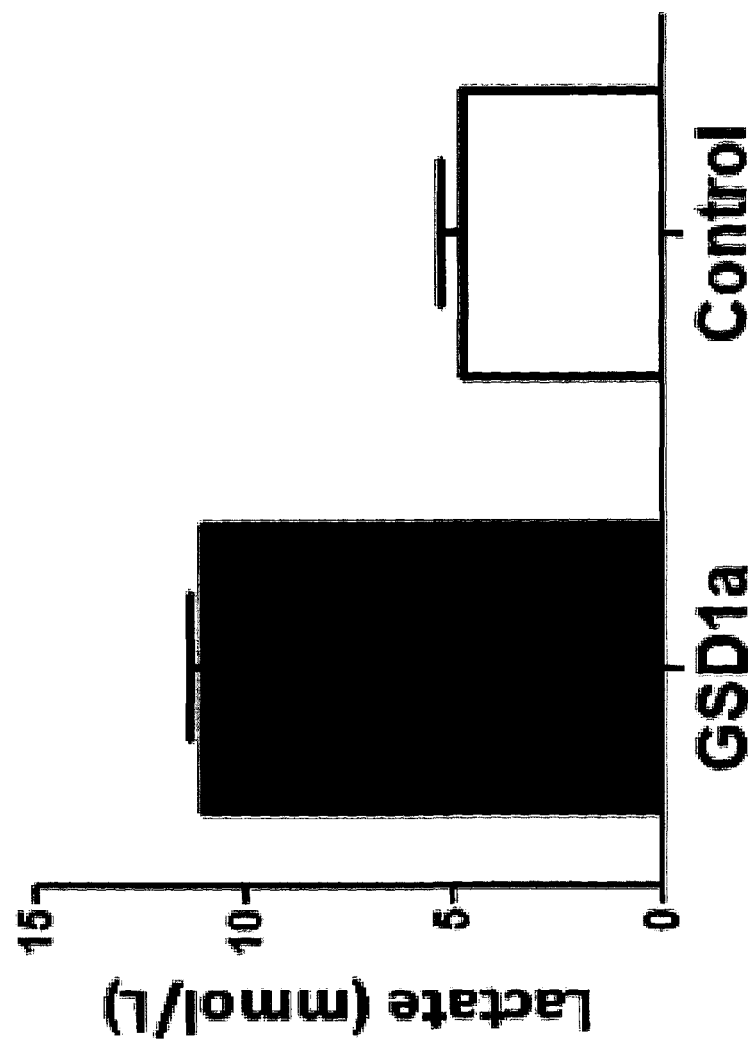

FIG. 17 shows GSD-dhIPSC derived hepatocytes (GSD1a) secrete more lactate (GSD1a) compared to hIPSC derived hepatocytes from control subjects (Control) when assessed by ELISA analysis of a 24 hour collection of cell culture medium. n=3

Figure 18:
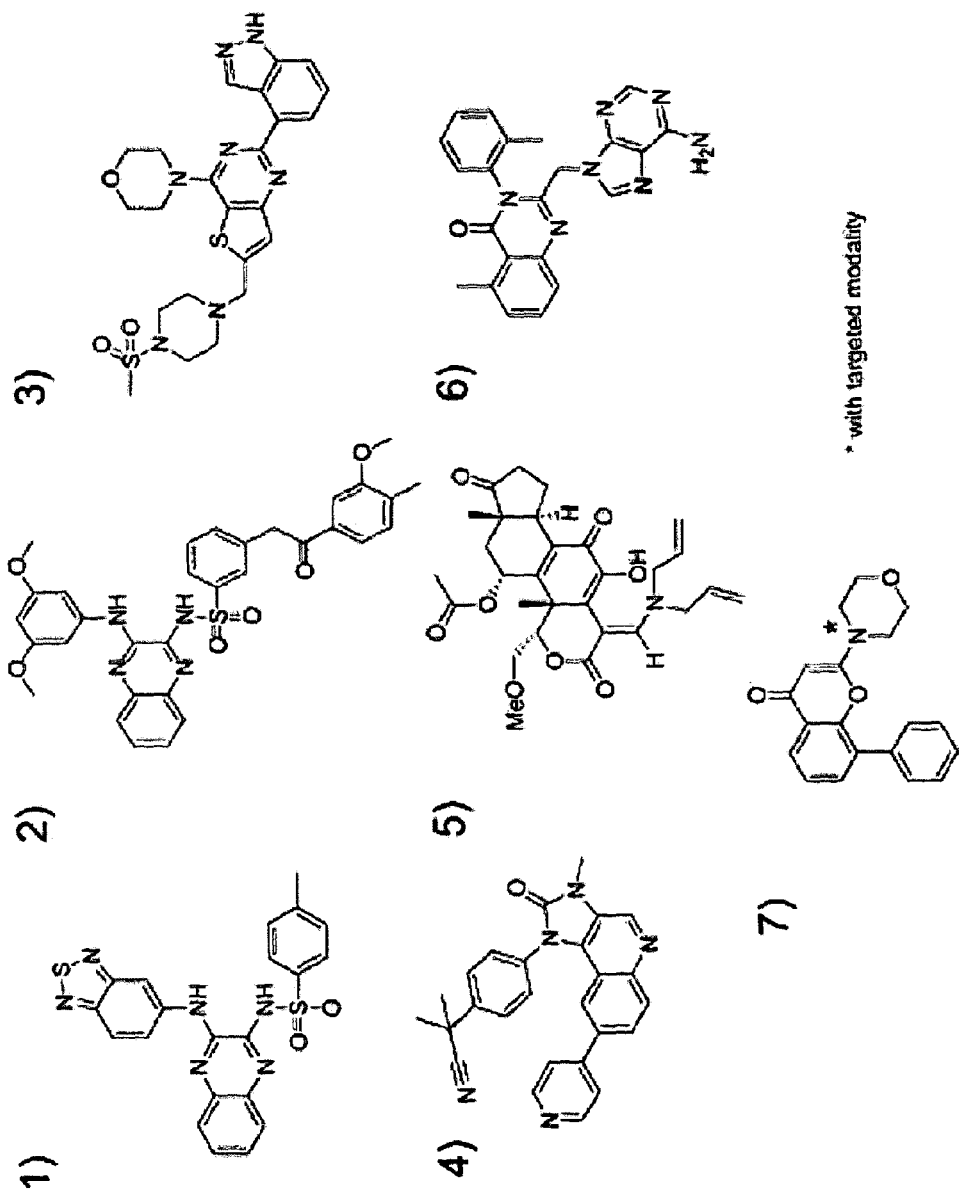

FIG. 18 shows examples of PI3K inhibitors.

Figure 19:
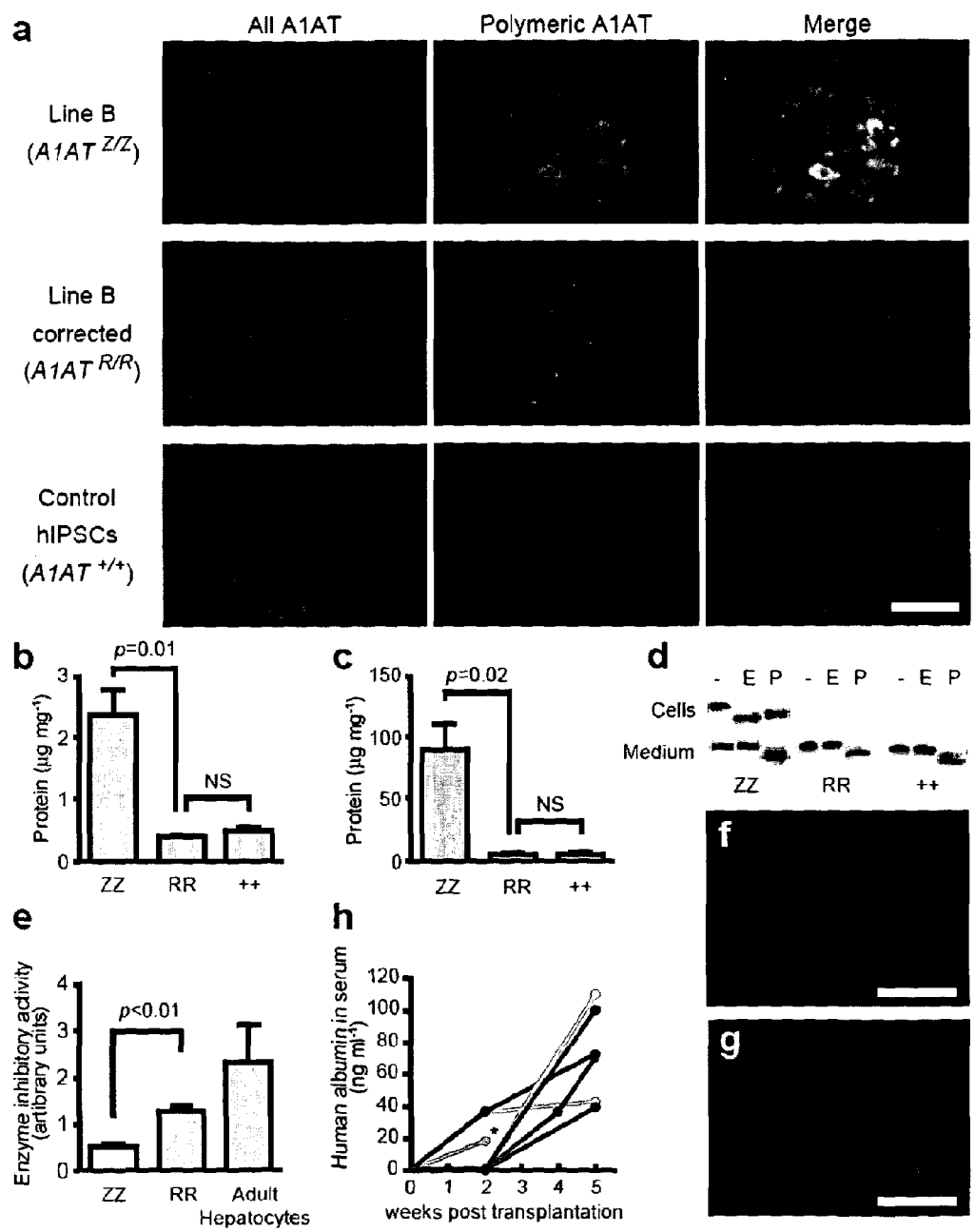

FIG. 19 shows functional analyses of restored A1AT in c-hIPSCs-derived hepatocyte-like cells. FIG. 19A shows immunofluorescence results showing the absence of polymeric A1AT protein in hepatocyte-like cells generated from c-hIPSCs. All forms of A1AT (left panels) and misfolded polymeric 12 A1AT (middle panels). FIGS. 19B and 19C show ELISA data to assess the intracellular (19B) and secreted (19C) levels of polymeric A1AT protein in hepatocyte-like cells derived from A1ATD-hIPSCs (ZZ), chIPSCs (RR) and control hIPSCs (++). FIG. 19D shows endoglycosidase H (E) and peptide:N-glycosidase (P) digestion of A1AT immunoprecipitated from uncorrected (ZZ), corrected (RR) and control (++) hIPSC-derived hepatocyte-like cells (upper panels) and corresponding culture medium (lower panels). FIG. 19E shows chymotrypsin ELISA showing that corrected cells (RR) have A1AT enzymatic inhibitory activity that is superior to uncorrected cells (ZZ) and close to adult hepatocytes. FIGS. 19F and 19G show immunofluorescence of transplanted liver sections detecting human albumin (FIG. 19F) and A1AT (FIG. 19G). DNA was counterstained with DAPI. FIG. 19H shows ELISA read-out of human albumin in the mouse serum longitudinally followed for each mouse. Asterisk, the mouse was subjected to histology analysis. Scale bars, 100 μm. Data in B, C and E are shown as mean±s.d. (n=3). Student's t-test was performed. NS, not significant.

EXPERIMENTS

Methods hIPSC Derivation and Culture

Following appropriate ethical approval and patient consent, 8 mm skin punch biopsies were obtained from volunteering patients attending Addenbrooke's Hospital (Ethics ref number 08/H0311/201; R&D No: A091485). Fibroblasts were derived from the donated tissue in GMP conditions using standardised in house protocols and expanded in standard fibroblast culture medium. Additional fibroblast samples were obtained from INSERM (France) and the Coriell Biorepository. In total 5 different disease samples from 7 different patients were obtained as detailed in Table 1. Moloney murine leukemia virus-derived vectors each containing the coding sequences of one of the four human genes, Oct-4, Sox2, c-Myc, and Klf4, and the corresponding viral particles were generated by Vectalys (Toulouse, France) and used to infect the fibroblasts at a multiple of infectivity of 10 as originally described by Yamanaka and colleagues and as we also recently described [29]. Once derived, hIPSCs were cultured in standard hESC culture conditions (knockout [KSR], (Gibco)+FGF2 (4 ng/ml; R&D Systems Inc., Minneapolis) on plates containing irradiated mouse feeders.

RNA Extraction and Real-time Polymerase Chain Reaction

Total RNAs were extracted from hIPSCs or differentiated progenitors using the RNeasy Mini Kit (Qiagen, Hilden, Germany). Each sample was treated with RNase-Free DNase (Qiagen) to avoid DNA contamination. For each sample 0.6 μg of total RNA was reverse transcribed using Superscript II Reverse Transcriptase (Invitrogen). Real-time polymerase chain reaction (PCR) reaction mixtures were prepared as described (SensiMiX protocol; Quantace, London) then denatured at 94° C. for 5 minutes and cycled at 94° C. for 30 seconds, 60° C. for 30 seconds, and 72° C. for 30 seconds, followed by a final extension at 72° C. for 10 minutes after completion of 40 cycles. Primer sequences are described elsewhere [16]. Real-time PCR reactions were performed using a Stratagene Mx3005P (La Jolla, Calif.) in triplicate and normalized to porphobilinogen deaminase (PBGD) in the same run. QPCR data are presented as the mean of three independent experiments and error bars indicate standard error of the mean. Primers used for Real Time PCR analyses are listed in the table at the end.

Immunofluorescence hIPSCs or their differentiated progenitors were fixed for 20 minutes at 4° C. in 4% paraformaldehyde and then washed three times in PBS. Cells were incubated for 20 minutes at room temperature in PBS containing 10% donkey serum (Serotec Ltd.) and subsequently incubated overnight at 4° C. with primary antibody diluted in 1% donkey serum in PBS as follows: Oct-4 (1:100; Abcam ab18976 [Cambridge, U.K.] Sox2 (1:100; Abcam ab15830), Brachyury (1:100; Abcam ab20680 or R&D Systems Inc.), Sox17 (R&D Systems Inc.), FoxA2 (1:50; Abcam ab5074), GATA4 (1:250; Santa Cruz Biotechnology Inc.), GATA6 (1:200; Abcam ab22600 or Santa Cruz Biotechnology Inc.), CXCR4 (1:100; R&D Systems Inc. or BD Pharmingen), CK18 (1:50, Dako) CK19 (1:50, Dako), Albumin (1:100; R&D1455), Alpha Fetoprotein (1:300, Dako A008), α1-antitrypsin (1:100, Sigma A0608) Cells were then washed three times in PBS and incubated with Texas Red or fluorescein isothiocyanate-conjugated anti-mouse IgG (Sigma-Aldrich; 1:200 in 1% donkey serum in PBS) or rabbit IgG (Jackson Laboratory, Bar Harbor, Me.; 1:400 in donkey serum in PBS) or goat IgG (Jackson Laboratory; 1:400 in donkey serum in PBS) for 2 hours at room temperature. Unbound secondary antibody was removed by three washes in PBS. Hoechst 33258 was added to the first wash (Sigma-Aldrich; 1:10,000). For lipid visualization a lipid specific stain BODIPY (boron-dipyrromethene; BODIPY® 493/503 Invitrogen. D-3922) was used.

Teratomas hIPSCs were harvested mechanically immediately prior to implantation, and approximately $10^6$ cells were inoculated beneath the testicular capsule of 8-week-old C.B.-17/GbmsTac-scidbgDFN7 male mice (Taconic M&B, ejby, Denmark) housed and maintained at 20° C.-24° C., 50% room humidity, in a 14- to 10-hour light-dark cycle with food and water libitum. The mice were sacrificed after 60 days and then the injected testes were cut into equal pieces using a razor blade. The material was fixed overnight in 4% neutral buffered formaldehyde, and dehydrated through a graded series of alcohols to xylene. The tissue was embedded in paraffin, serially sectioned at 5 μm, followed by H&E staining and characterization. A human origin of the selected areas was verified by fluorescent in situ hybridization (human-specific probes, CEP XY; Vysis Inc., Downers Grove, Ill.). The experiments were performed with permission from the Regional Committee for Animal Experimentation (Stockholm, Sweden; Dnr N107/06).

Karyotype Analysis.

hIPSCs were grown to confluency on 10 cm dishes then harvested and metaphase spreads obtained by the Cambridge University Hospitals Cytogenetics diagnostics laboratory.

Differentiation of hIPSCs to Hepatocytes hIPSCs were passaged using 5 mg/ml collagenase IV/dispase (0.1%, GIBCO) 1:1 (v/v) mix; then transferred onto plates pre-coated with fetal bovine serum (FBS) in CDM-PVA or in plates pre-coated with human fibronectin as previously described [16]. For the first following day, cells were grown in CDM-PVA supplemented with CHIR99021 (3 μM, Stemgent), Ly294002 (10 μM, Calbiochem), activin (100 ng/ml, R&D systems), FGF2 (40 ng/ml, R&D systems) and BMP4 (10 ng/ml, R&D systems) to drive differentiation of hIPSCs into primitive streak like cells. The next day, the resulting cells were grown in CDM-PVA supplemented with Ly294002 (10 μM, Calbiochem), activin (100 ng/ml), FGF2 (40 ng/ml, R&D systems) and BMP4 (10 ng/ml, R&D systems) to drive their differentiation toward definitive endoderm. On the third day the basal medium was changed to RPMI (Gibco 1640) and supplemented with activin (100 ng/ml, R&D systems), FGF2 (40 ng/ml, R&D systems) and B27 to obtain anterior definitive endoderm cells (ADE). To induce hepatic endoderm, ADE cells were then cultured for five days in the presence of RPMI (Gibco 1640) supplemented with Activin (50 ng/ml, R&D systems). Finally to mature the resulting hepatic progenitors, cells were grown in a CMRL/Hepatozyme (Invitrogen) basal medium supplemented by HGF (20 μg/ml, Peprotech) and Oncostatin-M (10 μg/ml, R&D).

Flow Cytometry

For detection of Albumin positive cells, adherent cells at the end of the hepatocyte differentiation protocol were washed twice in PBS and then incubated for 20 minutes at 37° C. in cell dissociation buffer (Invitrogen, Carlsbad, Calif.). Cells were dissociated by gentle pipetting and resuspended at approximately $0.1$-$1 \times 10^5$ cells per milliliter in PBS+3% normal goat serum (NGS) containing 0.1% azide (Serotec Ltd., Oxford, U.K.) and 0.1% Triton-X. Cells were then incubated for 40 minutes at 4° C. with primary mouse anti human Albumin antibody (R&D 1455; 1 in 100) or mouse IgG isotype control (BD Pharmingen). Cells were then analyzed by a FACS Calibur machine (BD Biosciences, San Jose, Calif., USA). Number of albumin positive cells was recorded as the average from three separate experiments.

Subcellular Fractionation Using Iodixanol (OptiPrep Axis Shield 2010) Stepped Gradient and EndoH Digestion.

dhIPSC derived hepatocytes were grown in 6 well plates and harvested using a cell scraper. Cells were then mechanically disrupted by repeated passage over a ball bearing homogenizer. The cell suspension was centrifuged at 3000 g for 5 minutes (4° C.) and the supernatant diluted to a final concentration of 35% OptiPrep and transferred to a new centrifuge tube.

2 ml of 30% OptiPrep and 1 ml of 0% Optiprep were carefully layered sequentially on top of the supernatant and the tube spun at 70,000 g for 2 hours (4° C.). The liquid interface formed between the two bottom layers was carefully aspirated and again spun at 100,000 g for 45 minutes (4° C.). The subsequent pellet formed was re-suspended in 50 μl of buffer and labelled as the microsomal fraction. For endoglycosidase H [EC 3.2.1.96, glycopeptide-D-mannosyl-N4-(N-acetyl-D-glucosaminyl)-2-asparagine 1,4-N-acetyl-b-glucosaminohydrolase] digestion, microsomal cellular fractions were digested with 500 units of EndoH enzyme (Boehringher Mannheim, Mannheim, Germany) for 3 hours at 37° C. then analyzed as detailed below.

SDS PAGE and Western Blot Analysis

Samples of 30 μl were mixed with 10 μl 4× loading buffer containing 10% (v/v) β-mercaptoethanol and 4% (w/v) SDS and analyzed by 8% (w/v) acrylamide SDS-PAGE. The proteins were transferred from the gels onto Immobilon P membrane (Millipore Corp., Bedford, Mass.) at 200 mA for 2 h for Western blot analysis. 20% (v/v) methanol was added to the transfer buffer. After transfer, the membrane was washed in PBT (PBS plus 0.1% (v/v) Tween 20) and blocked overnight in PBT plus 5% (w/v) dried skimmed milk powder. The following day, the membrane was incubated with anti-α1-antitrypsin antibody diluted 1:10,000 in PBT milk for 1 h, washed six times for 5 min with PBT, and then incubated with 1:100,000 anti-mouse IgG-horseradish peroxidase antibody in PBT-milk for 1 h. The membrane was washed a further six times for 5 min with PBT and 15 min in PBS before developing using the ECL Super Signal West Femto maximum sensitivity substrate (Pierce) and exposed to film.

Enzyme Linked Immunosorbant Assay (ELISA) for α1-antitrypsin

High binding surface COSTAR 96-well plates (Corning, N.Y., USA) were coated overnight with affinity-purified rabbit polyclonal antibodies against α1-antitrypsin (Abcam 31657, Cambridge, UK) at 2 μg/ml in carbonate/bicarbonate buffer ($Na_2CO_3$/$NAHCO_3$, pH 9.5). After washing (0.9% w/v NaCl, 0.05% v/v Tween 20), the plates were blocked for two hours in blocking buffer (PBS, 0.25% w/v BSA, 0.05% v/v Tween 20). Samples (culture medium or cells lysed in 50 μl of Nonidet lysis buffer (150 mM NaCl, 50 mM Tris-Cl, pH 7.5, 1% (v/v) Nonidet P-40), and standards (plasma purified M or Z α1-antitrypsin) were diluted in blocking buffer and 50 μl added to each well then incubated for two hours. After washing, the wells were incubated with either 9C5 or 2C1 monoclonal antibodies (1 μg/ml diluted in blocking buffer), and incubated for two hours. Bound monoclonal antibodies were detected with rabbit anti-mouse IgG HRP-labelled antibody (Sigma Aldrich, Haverhill, UK, 1:20,000) for one hour. The reaction was developed with TMB liquid substrate (Sigma Aldrich, Haverhill, UK) for 10 minutes in the dark and the reaction was stopped with 1 M $H2SO4$. Absorbance was read at 450 nm on a Thermo-max microplate reader (Molecular Devices, Sunnyvale, Calif., U.S.A.). For the proteosome blocking assay, cells were grown in 6 well plates and MG132

(AG Scientific, USA) diluted 1 in 10,000 was added to the culture medium 16 hours (overnight) prior to harvest. Control samples had equal volumes of PBS added to them.

Enzyme Linked Immunosorbant Assay (ELISA) for Albumin

Cell culture medium collected over 24 hrs was analyzed in triplicate by the Cambridge University Hospitals Biochemical diagnostics laboratory using an in house human albumin specific ELISA kit (BioSupply UK). Values were expressed as ng per million cells per ml of culture medium.

Cytochrome P450 Activity

Cyp3A4 activity assay was measured in triplicate using the P450-Glo assay kit (Promega) according to the manufacturer's instructions. Cytochrome activity was then analysed using a P450-GloMax 96 microplate luminometer.

Periodic Acid Schiff (PAS) Staining

PAS staining was carried out on cells in triplicate using a kit (Sigma 395B-1KT) under the guidance of manufacturer's instructions. Diastase digestion was subsequently performed to confirm the positive staining was due to presence of Glycogen.

Transmission Electron Microscopy (TEM)

Cells were rinsed briefly in 0.9% NaCl and fixed for 2 hours in 4% glutaraldehyde at 4° C. Cells were then scraped from the plates under fix and resuspended by rinsing in 0.1 M PIPES. Analysis was performed by TEM.

Uptake of LDL

The Dil-LDL staining kit was purchased from (Stoughton, Mass.) and the assay was performed according to the manufacturer's instructions. FACS analysis was performed comparing Dil incorporation in FH disease specific hIPSC hepatocytes with Dil incorporation in control (HepG2 cells).

GFP Reporter

Cells were transduced with the APOA-II-GFP lentivector as previously described [16] and examined by microscopy.

Metabolic Enzyme Response to Glucagon Stimulation dhIPSC derived hepatocytes were incubated for six hours in serum-free, high-glucose DMEM supplemented with 2 mM L-glutamine, 100 U/l penicillin, 100 ug/ml streptomycin, and 0.5% Bovine Serum Albumin (all from Sigma-Aldrich). Cells were stimulated with 100 nM glucagon 23 hydrochloride (Novo Nordisk, Bagsvard, Denmark) or PBS (Sigma-Aldrich) as a negative control. Total RNA was harvested using the RNeasy Kit (Qiagen, Hilden, Germany) at 0, 1, 2 or 3 hours after stimulation and purified as per manufacturer's guidelines. Reverse transcription was performed on 1 ug RNA in a 25 μl reaction mixture containing 2000 Moloney Murine Leukemia Virus Reverse Transcriptase, 500 ng random primers and 0.5 mM deoxynucleotide triphosphates (all from Promega, Wis., Ma) as per manufacturer's guidelines. cDNA was subjected to real-time quantitative PCR on an ABI7900 detection system (Applied Biosystems, Foster City, Calif.) using Taqman PCR Mastermix (Applied Biosystems) and gene-specific forward and reverse primers and fluorogenic probes. All results were normalised to human 36B4 as a reference gene. Primers and probes for PEPCK (Hs00159918_1), G6P (Hs00609178_1) and IGFBP1 (Hs00426285 ml) were purchased as premade stocks from Applied Biosystems. Oligonucleotides for 36B4 were designed in-house and synthesised by Sigma-Aldrich (Forward, 5'-GCAGATCCGCATGTCCCTT-3'; Reverse, 5'-TGTTTTCCAGGTGCCCTCG-3'; Probe, 5'-[JOEE]AG-GCTGTGGTGCTGATG[TAMRA]-3').

Correction of Z Mutation in A1ATD-hIPSCs

A1ATD-hIPSCs are described above. $2 \times 10^6$ hIPSCs were co-transfected with ZFN expression vectors and the donor template, and subjected to puromycin selection (1 μg ml-1) initiated 4 days after transfection. For transposon excision, targeted cells were transfected with pCMV-yPBase (Yusa, K., et al PNAS USA 108, 1531-1536 (2011)), cultured for 4 days, replated and selected in 250 nM 1-(2-Deoxy-2-fluoro-beta-D-arabinofuranosyl)-5-indouracil (FIAU). To increase clonogenicity, cells were treated with ROCK inhibitor[26], Y-27632 (10 μM) 4 hours prior to dissociation and 24 hours post plating. Resulting colonies were picked 2 weeks later, analyzed by PCR and further verified by Southern blot analysis.

hIPSCs-derived Hepatocyte-like Cell Transplantation in Immunodeficient uPA Transgenic Mice All mice were housed in pathogen-free conditions and animal studies were approved by the committee on animal experimentation of the Institut Pasteur and by the French Ministry of Agriculture. Differentiated cells ($5 \times 10^5$ cells per animal in 50 μl DMEM) were injected into the spleens of 3- to 4-week-old Alb-uPA+/+;Rag2-/-;Il2rg-/- mice (n=7). The recipient mouse was sacrificed 2 weeks after transplantation for histological analysis. Blood samples were collected and human albumin in plasma was quantified by ELISA (Bethy Laboratories). Frozen liver sections were analyzed by immunofluorescence with human albumin (Dako) or human A1AT (Dako) specific antibodies. Non-transplanted mice were used as controls.

Results 5 hIPSC-derived hepatocytes from affected patients were found to successfully recapitulate key features of the cellular pathology seen in the associated diseases, such as aggregation of misfolded mutant α1-antitrypsin in the endoplasmic reticulum, deficient LDL receptor-mediated cholesterol uptake and elevated cellular lipid and glycogen accumulation. These data demonstrate for the first time that hIPSCs can be used to model a diverse range of inherited diseases in adult cells.

Generation of a hIPSC Library from Patients with Inherited Metabolic Diseases of the Liver (IMDs)

Dermal fibroblasts were obtained from skin biopsies from seven individuals with a range of IMDs and three healthy controls (20 hIPSC lines, 7 patients, 5 diseases—Table 1). These somatic cells were then reprogrammed to pluripotent stem cells using the four factor approach developed by Yamanaka et al [13]. The success rate of hIPSC derivation was extremely variable ranging from 0.01% to 0.1% for each individual, confirming the existent variability in capacity to reprogram dermal fibroblasts from patients of different ages and sex. Where possible, 3 hIPSC lines per individual were subsequently used for further analyses in order to define the conserved variability in differentiation capacity existent between lines derived from the same individual. The resulting library of hIPSC lines (20 lines from 10 individuals) were characterized for their morphology, expression of pluripotency markers, capacity to form derivatives of the three germ layers in vivo and in vitro, normal karyotype and the expression profiles of endogenous and exogenous pluripotency genes.

All the hIPSCs expressed endogenous markers of pluripotency and were able to differentiate into neuroectoderm, endoderm and mesoderm cells, confirming that we were able to generate pluripotent stem cells from somatic cells. Interestingly, none of the hIPSC lines lacked the ability to differentiate into one specific germ layer showing the absence of strong variability in the capacity of differentiation of the hIPSC lines generated for this study. Furthermore, abnormal karyotype was only observed in hIPSCs grown for long periods of time (passage 40) in chemically defined conditions. This suggests that the culture system used to expand hIPSCs can affect their genetic stability as had been described for human Embryonic Stem Cells (hESCs) [14]. Therefore, only "early passage" hIPSCs (<p30) were used for this study. The number of viral integrations was variable between lines and patients reinforcing previous studies showing that full reprogramming is not associated with a specific pattern of viral integration [15].

Finally, ectopic expression of exogenous transgenes was rarely detected in our hIPSCs lines demonstrating the efficiency of our viral vector to be silenced in pluripotent stem cells. Collectively these results demonstrate that the hIPSC lines generated for this study were fully reprogrammed and thus represent a unique library of hIPSC lines derived from patients with IMDs.

Development of a Robust and Simple Method to Generate Hepatocytes from Patient Specific hIPSCs We have recently developed a robust protocol to differentiate human ES and normal hIPSCs into hepatocytes [16]. This culture system provided the basis for a novel method of differentiation, optimal for use with patient specific hIPSCs. Our main objective was to develop a simple method that could effectively differentiate a broad number of hIPSC lines into hepatocytes. hIPSC lines derived from healthy individuals (n=6; 2 different subjects) and individuals with α1-antitrypsin deficiency (n=6; 3 different patients) were used to empirically screen a wide range of culture conditions.

Figure 1:
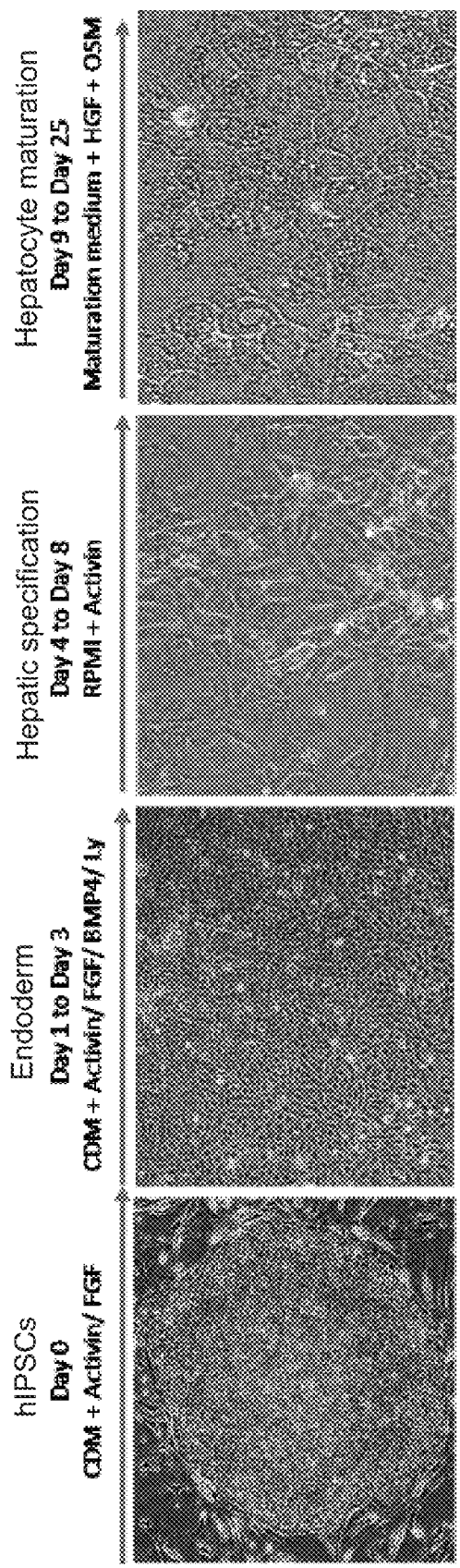
FIGS. 1 to 5 show the generation of hepatocytes from disease specific hIPSCs (dhIPSCs).

The resulting protocol is described in FIG. 1. This three step protocol follows the key stages of the natural pathway of hepatocyte development. The first step consists of driving hIPSCs to endoderm cells expressing Sox17, CXCR4, foxA2 and Hex, a specific marker of anterior definitive endoderm from which the liver cells are generated (FIGS. 1b and 1c) using CDM-PVA medium supplemented with Activin, FGF2, BMP-4 and a PI3 Kinase inhibitor. The resulting endoderm cells are then differentiated into hepatic progenitors expressing AFP, CK18, CK19, HNF4, and HNF6 (FIG. 2, 3) using Activin and B27 supplement.

Finally maturation in a CMRL/Hepatocyte culture medium mix supplemented with hepatocyte growth factor (HGF) and oncostatin-M yielded hepatocyte-like cells expressing both albumin and α1-antitrypsin by day 25 (FIGS. 2, 3 and 4). FACS analyses showed that 80% of the cells generated in these culture conditions expressed albumin (FIG. 4) confirming the homogeneity of the cell population generated with this approach. By day 25, the cells showed a strong morphological resemblance to human hepatocytes, displaying occasional binucleity (FIG. 1), glycogen deposits & apical microprotrusions (FIG. 5), rough and smooth endoplasmic reticulum (ER) and a prominent golgi body. In addition, the hIPSC derived hepatocytes shared similar in vitro functional characteristics to native human hepatocytes in that they were able to store glycogen & LDL, secrete albumin, metabolize drugs via the CytP450 pathway (FIG. 6) and express GFP protein under the control of the hepatocyte specific ApoAII promoter.

Furthermore, the expression of exogenous reprogramming factors remained suppressed in these cells confirming that the retroviral transgenes stay silenced after differentiation.

Whilst these data provide considerable evidence showing relevant functional characteristics of the liver cells generated in our culture system, we acknowledge that these cells were not terminally differentiated as evidenced by their continued expression of AFP (FIGS. 2 & 3). Instead, these hepatocytes are likely to be developmentally located somewhere between the end of the first trimester of foetal embryonic development and fully adult cells as displayed by their α1-antitrypsin gene expression levels and percentage of Albumin expressing cells seen by FACs (FIG. 1d).

Liver cells generated in our culture system express hepatocyte markers such as albumin (ALB), α-1-antitrypsin (AAT), αAPOF, TAT, TDO2, TTR, HNF4α and HHEX (FIG. 4A). The expression of foetal markers, such as alpha-Fetoprotein (AFP) and CYP3A7 was also maintained throughout the differentiation process while the expression of the adult cytochrome CYP3A4 remained relatively low (FIG. 4A), suggesting that these cells represent foetal-like hepatocytes and that further maturation would be necessary for generating adult cells. These observations were confirmed by immunostaining and FACS analyses, which showed homogenous co-expression of ALB, cytokeratin 18, AAT and AFP (FIGS. 4B and 4C). However, these cells also displayed functional characteristic of hepatocytes such as: (i) ALB and AAT secretion (FIG. 4D), (ii) Cyp3A4 activity inducible by dexamethasone (FIG. 4E), (iii) cholesterol up take and (iv) glycogen storage (FIG. 4F).

Finally, we observe that this culture system was applied to a large number of lines (20 hIPSC lines from 10 individuals) and only 2 hIPSC lines were unable to differentiate into liver cells.

Collectively, these results demonstrate the efficiency of our defined culture conditions for driving differentiation of hIPSCs to near homogenous populations of foetal hepatic cells displaying some functional characteristics specific to mature hepatocytes.

In vitro Modelling of Liver Diseases Using Patient Specific hIPSCs: α1-Antitrypsin Deficiency The validity of our approach to model liver disease in vitro was assessed by investigating whether the disease specific hIPSC (dhIPSC) derived hepatocytes were able to replicate key features of the diseases from which they were derived. We first focussed on α1-antitrypsin deficient dhIPSCs. Previous studies have shown that the Z allele (Glu342Lys) results in the formation of ordered polymers of α1-antitrypsin that are retained within the ER [17]. These polymers accumulate within hepatocytes, predisposing the homozygote to neonatal hepatitis, cirrhosis, and hepatocellular carcinoma [18]. This pathway of α1-antitrypsin polymerisation is central to the clinical phenotype [17]. We therefore used the 2C1 polymer specific monoclonal antibody [30] to detect polymers within α1-antitrypsin deficient dhIPSC derived hepatocytes. Polymers were detected by immunostaining (FIG. 8) and by ELISA (FIG. 10) analyses. These data show that accumulation of α1-antitrypsin polymers only occurred in dhIPSC derived hepatocytes from individuals with α1-antitrypsin deficiency. No polymers were present in hIPSC derived hepatocytes from control subjects. The cellular localization of the polymers was confirmed by subcellular fractionation of the cells followed by digestion with endoglycosidase H (FIG. 9), an enzyme which removes N-linked glycans that are still in the high mannose ER form but does not affect oligosaccharide chains after the addition of sialic acid in the Golgi apparatus.

Endoglycosidase H treatment reduced all intracellular α1-antitrypsin in the patient specific but not control hIPSC derived hepatocytes to a single 50-kDa band demonstrating that all such intracellular α1-antitrypsin was retained within the ER. Importantly, the observed increase in polymer was consistent between three different hIPSC lines taken from the same patient but varied between hIPSC lines taken from different patients. This phenotypic variability could correlate with the disease status in the patient and thus could reflect a clinical feature of this disease. However, low level of polymer expression was observed in hIPSC lines derived from A1ATD patient 2 which were also particularly resistant to endoderm differentiation. Therefore, variability in disease phenotype observed in this study mainly reflects the capacity of hIPSCs to achieve efficient hepatic differentiation.

Finally to investigate the potential application of this cell line for future in vitro drug screening we assessed the effects of adding the proteasome inhibitor (MG132) to the medium overnight. Blockage of this important protein degradation pathway revealed a disease specific intracellular increase in α1-antitrypsin polymers (FIG. 10). Taken together these results demonstrate that dhIPSC-derived hepatocytes are capable of modelling key pathological feature of α1-antitrypsin deficiency in vitro and may also prove useful for future drug screening assays.

In vitro Modelling of Liver Diseases Using Patient Specific hIPSCs: Familial Hypercholesterolaemia To confirm the ability of our culture system to model clinical disease, and to investigate its potential for studying disease processes specific to other subcellular locations, we characterised the dhIPSC derived hepatocytes from one individual with Familial Hypercholesterolaemia (FH). The primary defect in FH is impaired functioning of the LDL receptor resulting in an excess of plasma LDL and premature atheromas [19]. dhIPSC lines generated from the individual with FH were differentiated into hepatocytes displaying typical functional characteristics (FIG. 11). Western blot analysis of the differentiated cells confirmed the absence of the LDL receptor.

The in vivo functional implications of this receptor deficiency were also conserved in our model as shown by immunostaining and FACS analysis demonstrating FH-dhIPSCs derived hepatocytes had an impaired ability to incorporate LDL (FIG. 12). These results demonstrate that dhIPSCs can successfully be used to model FH and may therefore be suitable for modelling other diseases involving transmembrane protein trafficking and receptor dysfunction.

In vitro Modelling of Liver Diseases Using Patient Specific hIPSCs: Glycogen Storage Disease Type 1a (GSD-1a)

Finally, we used our approach to model a condition representative of impaired cytosolic metabolism. GSD-1a is caused by a deficiency in glucose-6-phosphatase, the main enzyme catalyzing the hydrolysis of glucose-6-phosphate to glucose and phosphate, the terminal steps in gluconeogenesis and glycogenolysis. Individuals with GSD-1a cannot maintain glucose homeostasis and experience hyperlipidemia, lactic acidosis, hyperuricemia, hypoglycemia, hepatomegaly, kidney enlargement and growth retardation [20]. Three GSD-1a lines derived from one subject were differentiated and the resulting cells characterised for their hepatocyte like nature (FIG. 13).

Confirmation of the cellular disease phenotype was seen following Period acid Schiff staining which revealed the GSD1a dhIPSC derived hepatocytes accumulated significantly greater amounts of intracellular glycogen compared to control (FIG. 14). In addition the same cells also replicated other features of the disease such as excessive lipid accumulation (FIG. 15) and excessive production of lactic acid (FIG. 17). Critically the cells exhibited induction of expression of three canonical glucagon-responsive genes after glucagon stimulation (FIG. 16) [21] [22]. These results demonstrate not only that key cellular aspects of GSD1a can be modelled in vitro, but also that the hepatocytes generated in our culture system display at least some responsiveness to a key hormone of intermediary metabolism, suggesting our approach could therefore be applied to model other more common metabolic disorders.

By developing a simple chemically defined culture system permitting efficient differentiation of numerous hIPSC lines towards cells of a mature hepatic state, we have demonstrated the modelling of groups of diseases of non-neuronal origin whose phenotypes are a consequence of complex protein dysregulation within adult cells. The three diseases we modelled encompass a diverse range of pathological mechanisms from protein misfolding in the ER, to cell surface receptor dysfunction and finally obstruction of cytosolic metabolism, thereby demonstrating the potentially wide applications for exploitation of this new platform into other research areas.

The potential of our modelling system is best exemplified by first considering the most common and well characterized disorder from our group of diseases, α1-antitrypsin deficiency. Previous studies have demonstrated that misfolding and entrapment of the Z polymers within the ER is the underlying mechanism for the clinical phenotype. [17] However the variation in phenotype displayed between individuals with the same genotype has not yet been explained. Such variations may be due to different patient's capacities to handle misfolded proteins [23] [24] [8] [9, 18] [7]. The hepatocyte specific quality control mechanisms responsible for processing such proteins are now being elucidated [25, 26]. Although one such pathway, the proteosome, has an important role in metabolising Z α1-antitrypsin in some hepatic [27] and extrahepatic mammalian cell lines [28] it can only approximate protein handling in the proteosome of the human hepatocyte. Furthermore, despite our increased understanding of the protein degradation pathway, it still remains unclear how the accumulation of Z α1antitrypsin causes cell death and liver failure. In order to enhance our understanding of this and other related mechanisms critical to the aetiology of similar protein misfolding disorders, elucidation of the protein degradation pathways specific to human hepatocytes is a crucial next stage of investigation. By generating patient specific hIPSC derived hepatocytes capable of conserving core elements of disease specific protein polymerisation and ER entrapment, we show here that such subtle intracellular processes can potentially be studied with this novel in vitro cellular system.

Furthermore, our data also provide indication that the same intracellular processes may be accurately preserved despite the highly stressful implications that ex vivo reprogramming and differentiation protocols may have exerted upon the cells. [8, 24].

The two other diseases subsequently assessed with our modelling system reinforced the demonstration that downstream effects of protein dysfunction in hepatocytes are conserved within a patient specific manner using dhIPSCs. Firstly by replicating the lack of LDL receptor mediated uptake of LDL lipid into hepatocytes we successfully established a new cell model for Familial Hypercholesterolemia. The FH model illustrates how this platform is uniquely equipped to provide a holistic impression of the hepatocyte specific native processes governing receptor dysfunction, from nuclear synthesis to trafficking through the ER and ultimately recycling at the cell membrane. This platform may be well suited for further follow up studies into a broad range of liver related receptoropathies.

Correction of Genetic Defects in hIPSC Derived Hepatocytes

We next corrected a mutation in hIPSCs derived from individuals with α1-antitrypsin deficiency (A1ATD) using piggyback transposons (Yusa et al (2011) PNAS USA 108 1531-1536; Wang et al (2008) 105 9290-9295). A1ATD is an autosomal recessive disorder found in 1 out of 2000 individuals of North European descent and represents the most common inherited metabolic disease of the liver (Perlmutter, D. H. *Cell Death Differ* 16, 39-45 (2009); Gooptu, B. & Lomas, D. A. *Annu Rev Biochem* 78, 147-176 (2009)). It results from a single point mutation in the A1AT gene (the Z allele;

Glu342Lys) that causes the protein to form ordered polymers within the endoplasmic reticulum of hepatocytes. The resulting inclusions cause cirrhosis, for which the only current therapy is liver transplantation. The increasing shortage of donors and harmful effects of immunosuppressive treatments impose major limitations on organ transplantation, making the potential of hIPSC-based therapy highly attractive. We employed ZFN technology, which stimulates gene targeting in hESCs as well as hIPSCs (Urnov, F. D. et al. *Nat Rev Genet* 11, 636-646 (2010). Hockemeyer, D. et al. *Nat Biotechnol* 27, 851-857 (2009); Zou, J. et al. *Cell Stem Cell* 5, 97-110 (2009)). ZFN pairs were designed to specifically cleave the site of the Z mutation. A targeting vector was constructed from isogenic DNA with piggyBac repeats flanking the PGK-puroΔtk cassette. To minimize the distance between the mutation and the piggyBac transposon, a CTG leucine codon, 10 bp upstream of the mutation, was altered to a TTA leucine codon, generating the TTAA sequence, which would be left in the genome following piggyBac excision.

Puromycin-resistant hIPSC colonies obtained after co-electroporation of ZFN expression vectors and the targeting vector were screened for targeted clones by PCR. A1ATD-hIPSC lines derived from 3 different patients yielded targeted clones (Table 4). Remarkably, 54% of the puromycin-resistant colonies were targeted on one allele, while 4% were the result of simultaneous targeting of both alleles.

To remove the piggyBac-flanked selection cassette from these modified clones, we transiently transfected two homozygously targeted clones (B-16 and C-G4) with a hyperactive form of the piggyBac transposase (Yusa et al (2011) supra) and subjected them to FIAU selection. The genotype of the resulting FIAU-resistant colonies was analyzed by PCR and confirmed by Southern blot. Bi-allelic excision was observed in 11% of FIAU-resistant colonies (Table 5). Sequence analyses demonstrated that the Z mutation was corrected on both alleles and that transposon excision yielded a TTAA sequence as initially planned. The resulting corrected A1ATD-hIPSC (c-hIPSC) lines maintained the expression of pluripotency markers for more than 20 passages and their abilities to differentiate into cells expressing markers of the three germ layers, demonstrating that genome modification did not alter the pluripotency of c-hIPSCs.

We analyzed the genomic integrity of the hIPSC lines using comparative genomic hybridization (CGH). Two out of three A1ATD-hIPSC primary lines differed from their parental fibroblasts, showing amplifications or deletions ranging from 20 kb to 1.3 Mb, including a gain of 20q11.21, a frequently amplified region in hESCs (Lefort, N. et al. *Nat Biotechnol* 26, 1364-1366 (2008); Spits, C. et al. *Nat Biotechnol* 26, 1361-1363 (2008)). Line A retained a normal genome content compared to its parental fibroblast. Reassuringly, we found that after ZFN stimulated targeting, four out of six homozygous clones had unaltered genomes compared to their parental hIPSC lines. Sixteen cell lines with bi-allelic piggyBac excision were compared with their corresponding primary hIPSCs and 12 had unaltered genomes. We also analyzed the hIPSC lines by SNP arrays to check for loss of heterozygosity and found that all lines analyzed retained heterozygosity throughout their genome. This observation demonstrates that bi-allelic gene correction was the result of simultaneous homologous recombination followed by simultaneous excision at both alleles and that mitotic recombination was not involved in this process.

We sequenced exomes of the corrected B-16-C2 line and its parental fibroblast. Comparison of these exomes identified 29 mutations. The genesis of these mutations was determined by analysis of the primary hIPSC line and the homozygously targeted intermediate. Twenty-four point mutations and one 1-bp deletion were detected in the primary hIPSC line and four mutations arose during genetic correction: one during targeting and three during piggyBac excision. These mutations appeared to arise during culture since their genomic signatures were inconsistent with ZFN off-target sites or piggyBac integration sites. Taken together, we conclude that the combination of ZFNs with piggyBac allows rapid and clean correction of a point mutation in hIPSCs without affecting their basic characteristics.

To confirm that the genetic correction of hIPSCs resulted in the expected phenotypic correction, hIPSCs were differentiated in vitro into hepatocyte-like cells, the main cell type affected by the disease A1ATD. Differentiation of the corrected lines occurred as expected, resulting in a near homogenous population of hepatocyte-like cells.

Remarkably, CGH analysis of differentiated cells showed that hepatic differentiation neither increases the number of genetic abnormalities nor selects for cells with abnormal karyotype. The resulting cells shared key functional attributes of their in vivo counterparts including glycogen storage, LDL-cholesterol uptake, albumin secretion and cytochrome P450 activity. Importantly, immunofluorescence and ELISA both confirmed the absence of mutant polymeric A1AT in c-hIPSCs-derived hepatocyte-like cells that instead efficiently secreted normal endoglycosidase-H-insensitive monomeric A1AT (FIG. 19A-D). In addition, secreted A1AT displayed an enzymatic inhibitory activity that was comparable to that obtained from normal adult hepatocytes (FIG. 19E), thereby indicating that physiological restoration of enzyme inhibitory activity could be achieved.

Finally, the in vivo function of c-hIPSCs-derived hepatocyte-like cells (B-C16-2 line) was assessed following transplantation into the liver of Alb-uPA+/+;Rag2−/−;Il2rg−/− mice via intrasplenic injection. Livers harvested 14 days after injection were found to be colonized by human cells identified using antibodies specific to human albumin and A1AT (FIG. 19F, G). These human hepatocyte-like cells were distributed throughout the liver lobes and were seen to be integrated into the existing mouse parenchyma (FIG. 19F, G). In addition, human albumin was detected in the serum of transplanted animals for at least 5 weeks (FIG. 18H), while no tumour formation was detected in any mice. Therefore, c-hIPSCs-derived hepatocyte-like cells were able to colonize the liver in vivo and display functional activities characteristic of their human ESC-derived counterparts (Touboul, T. at al. *Hepatology* 51, 1754-1765 (2010)). Collectively, these analyses demonstrate that genetic correction of the Z mutation resulted in functional restoration of A1AT in patient-derived cells.

The experimental evidence above demonstrates the applicability of genetic correction in patient-specific iPSCs for cell-based therapy of A1ATD. The genetic correction was repeated in more clinically relevant cells using patient-specific iPSCs reprogrammed from fibroblasts with Sendaiviral vectors, an integration-free method (Fusaki, N., et al. *Proc Jpn Acad Ser B Phys Biol Sci* 85, 348-362 (2009)). A primary hIPSC line with an intact genome by CGH analysis was corrected by the method described above. The final product, iPSC-3-G5-A7, had the corrected A1AT, had an intact genome compared to the parental fibroblast, and expressed normal A1AT protein when differentiated to hepatocyte-like cells. This is the first demonstration of the generation of mutation-corrected patient-specific iPSCs.

The corrected iPSCs efficiently differentiated to hepatocyte-like cells and engrafted into an animal model for liver injury without tumour formation. In addition, hIPSCs derived from different patients were found to be effectively corrected, demonstrating that this method could be applied to a large number of A1ATD-hIPSC lines. Since the bi-allelic correction could be carried out in less than 4 months, our approach may be compatible with large-scale production of corrected patient-specific hIPSCs not only for A1ATD but also for other monogenic disorders.

In conclusion, this study has advanced the hIPSC field in several ways. Firstly, demonstration of the possibility of modelling different diseases affecting adult cells using a single platform has answered one of the most pressing questions in the hIPSC-disease modelling field. This realization has accordingly allowed us to provide a robust and easily reproducible technical resource for potential application into diverse fields of research. Secondly by demonstrating hIPSC derived hepatocytes can be generated from multiple patients of varied genetic and disease backgrounds, our system is shown to be an efficient new methodology for the early stage safety and therapeutic screening of liver targeted compounds of potential relevance to the pharmaceutical industry. Finally and perhaps most importantly, demonstrating the ability to homogenously derive large numbers of patient specific hepatocytes from a group of diseases ideal for cell based therapy, demonstrates that we have again taken another significant step towards the provision of patient specific hIPSC technology.

REFERENCES

1. Saha, K. and R. Jaenisch Cell Stem Cell, 2009. 5(6): p. 584-595.
2. Park, I. H. Cell, 2008. 134: p. 877-886.
3. Maehr, R., et al. PNAS 2009. 106(37): p. 15768-15773.
4. Dimos, J. T. Science, 2008. 321: p. 1218-1221.
5. Lee, G., et al. Nature, 2009. 461(7262): p. 402-406.
6. Ebert, A. D Nature, 2009. 457: p. 277-280.
7. Balch, W. E., et al. Science, 2008. 319(5865): p. 916-919.
8. Pan, S., et al. Hepatology, 2009. 50(1): p. 275-281.
9. Perlmutter, D. H. Cell Death Differ, 2008. 16(1): p. 39-45.
10. Enns, G. M. et al Molecular Genetics & Metabolism. 95(1-2): 3-10.
11. Fisher, R. A. et al Transplantation, 2006. 82(4): p. 441-9.
12. Guillouzo, A. et al Expert Opinion on Drug Metabolism & Toxicology, 2008. 4(10): 1279-1294.
13. Takahashi, K. and S. Yamanaka Cell, 2006. 126: p. 663-676.
14. Brons, I. G., et al Nature, 2007. 448(7150): p. 191-5.
15. Chin, M. H., et al. Cell Stem Cell, 2009. 5(1): p. 111-123.
16. Touboul, T., et al. Hepatology, 2009. 9999(999A): p. NA.
17. Gooptu, B. et al Ann. Rev. Biochem. 2009. 78(1): p. 147-176.
18. Perlmutter, D. H. Pediatr Res, 2006. 60: p. 233-238.
19. Rader, D. J. et al J. Clin. Invest. 2003. 111(12): p. 1795-1803.
20. Shieh, J.-J., et al. J. Biol. Chem. 2002. 277(7): p. 5047-5053.
21. Salayert, A. et al. J. Biol. Chem. 1982. 257(22): p. 13404-13412.
22. Dentin, R., et al. Nature, 2007. 449(7160): p. 366-369.
23. Piitulainen, E., et al Chest, 2005. 128: p. 2076-2081.
24. Wu, Y., et al. Proc Natl Acad Sci USA, 1994. 91: p. 9014-9018.
25. Cabral, C. M., et al J. Biol. Chem 2000. 275(32): p. 25015-25022.
26. Cabral, C. M., et al. Mol. Biol. Cell, 2002. 13(8): p. 2639-2650.
27. Teckman, J. H., et al. J. Biol. Chem 2001. 276(48): p. 44865-44872.
28. Qu, D., et al. J. Biol. Chem., 1996. 271(37): p. 22791-22795.
29. Vallier, L., et al. Stem Cells, 2009. 9999(999A): p. N/A.
30. Miranda, E., et al., (in press—Hepatology)

TABLE 1

| Gene | Sequence (5' to 3') |
|---|---|
| Exogenous hOCT4 | F: CCTCACTTCACTGCACTGTA<br>R: TCCTGTCTTTAACAAATTGGACT |
| Exogenous hKLF4 | F: GATGAACTGACCAGGCACTA<br>R: TCCTGTCTTTAACAAATTGGACT |
| Exogenous hSOX2 | F: CCCAGCAGACTTCACATGT<br>R: TCCTGTCTTTAACAAATTGGACT |
| Exogenous hMYC | F: AAGAGGACTTGTTGCGGAAA<br>R: TCCTGTCTTTAACAAATTGGACT |
| Endogenous hOCT4 | F: CCTCACTTCACTGCACTGTA<br>R: CAGGTTTTCTTTCCCTAGCT |
| Endogenous hKLF4 | F: GGTCGGACCACCTCGCCTTACAC<br>R: CTCAGTTGGGAACTTGACCA |
| Endogenous hSOX2 | F: ATGTCCCAGCACTACCAGAG<br>R: GCACCCTCCCATTTCCC |
| Endogenous hMYC | F: CTGAAGAGGACTTGTTGCGGAAAC<br>R: TCTCAAGACTCAGCCAAGGTTGTG |
| NANOG | F: CATGAGTGTGGATCCAGCTTG<br>R: CCTGAATAAGCAGATCCATGG |
| SOX17 | F: CAGTGACGACCAGAGCCAGACC<br>R: CCACGACTTGCCCAGCATCTT |
| FOXA2 | F: ACTCGCTCTCCTTCAACG<br>R: CCTGGTAGTAGGAGGTATCTGC |
| PBGD | F: GGAGCCATGTCTGGTAACGG<br>R: CCACGCGAATCACTCTCATCT |
| HEX | F: CACCCGACGCCCTTTTACAT<br>R: GAAGGCTGGATGGATCGGC |
| AFP | F: AGAACCTGTCACAAGCTGTG<br>R: TGGTAGCCAGGTCAGCTAAA |
| ALBUMIN | F: CCTTTGGCACAATGAAGTGGGTAACC<br>R: GACAGCAAGCTGAGGATGTC |
| AAT | F: AGACCCTTTGAAGTCAAGCGACC<br>R: CCATTGCTGAAGACCTTAGTGATGC |
| CYP3A4 | F: TGTGCCTGAGAACACCAGAG<br>R: GTGGTGGAAATAGTCCCGTG |
| ApoA2 | F: GGAGAAGGTCAAGAGCCCAGAG<br>R: AGCAAAGAGTGGGTAGGGACAG |
| LDLR | F: GGGCGTGAAATTGCGCTGGACCGTC<br>R: TCACAGACGAACTGCCGAGAGATGC |

TABLE 2

| COMPONENT | g/L |
|---|---|
| INORGANIC SALTS | |
| Ca(NO$_3$)$_2$•4H$_2$O | 0.1 |
| MgSO$_4$ (anhyd) | 0.04884 |
| KCl | 0.4 |
| NaHCO$_3$ | 2.0 |

TABLE 2-continued

| COMPONENT | g/L |
|---|---|
| NaCl | 6.0 |
| Na₂HPO₄ (Anhyd) | 0.8 |
| AMINO ACIDS | |
| L-Arginine (free base) | 0.2 |
| L-Asparagine (anhyd) | 0.05 |
| L-Aspartic Acid | 0.02 |
| L-Cystine•2HCl | 0.0652 |
| L-Glutamic Acid | 0.02 |
| L-Glutamine | 0.3 |
| Glycine | 0.01 |
| L-Histidine (free base) | 0.015 |
| Hydroxy-L-Proline | 0.02 |
| L-Isoleucine | 0.05 |
| L-Leucine | 0.05 |
| L-Lysine•HCl | 0.04 |
| L-Methionine | 0.015 |
| L-Phenylalanine | 0.015 |
| L-Proline | 0.02 |
| L-Serine | 0.03 |
| L-Threonine | 0.02 |
| L-Tryptophan | 0.005 |
| L-Tyrosine•2Na•2H₂O | 0.02883 |
| L-Valine | 0.02 |
| VITAMINS | |
| D-Biotin | 0.0002 |
| Choline Chloride | 0.003 |
| Folic Acid | 0.001 |
| myo-Inositol | 0.035 |
| Niacinamide | 0.001 |
| p-Amino Benzoic Acid | 0.001 |
| D-Pantothenic Acid•½Ca | 0.00025 |
| Pyridoxine•HCl | 0.001 |
| Riboflavin | 0.0002 |
| Thiamine•HCl | 0.001 |
| Vitamin B-12 | 0.000005 |
| OTHER | |
| D-Glucose | 2.0 |
| Glutathione (reduced) | 0.001 |
| HEPES | — |
| Phenol Red•Na | 0.0053 |
| ADD | |
| NaHCO₃ | — |

TABLE 3

| Components | g/L |
|---|---|
| L-Alanine | 0.025 |
| L-Arginine | 0.05787 |
| L-Aspartic Acid | 0.03 |
| L-Cysteine•HCl•H₂O | 0.26 |
| L-Cystine | 0.02 |
| L-Glutamic Acid | 0.075 |
| L-Glutamine | 0.1 |
| Glycine | 0.05 |
| L-Histidine HCl•H₂O | 0.02 |
| Trans-4-Hydroxy-L-Proline | 0.01 |
| L-Isoleucine | 0.02 |
| L-Leucine | 0.06 |
| L-Lysine•HCl | 0.07 |
| L-Methionine | 0.015 |
| L-Phenylalanine | 0.025 |
| L-Proline | 0.04 |
| L-Serine | 0.025 |
| L-Threonine | 0.03 |
| L-Tryptophan | 0.01 |
| L-Tyrosine | 0.04 |
| L-Valine | 0.025 |
| L-Ascorbic Acid | 0.05 |
| PABA | 0.00005 |
| D-Biotin | 0.00001 |
| Choline Chloride | 0.0005 |
| Coenzyme A•Na | 0.0025 |
| Cocarboxylase | 0.001 |
| 2'-Deoxyadenosine | 0.01 |
| 2'-Deoxyguanosine | 0.01 |
| 2'-Deoxycytidine•HCl | 0.0116 |
| Flavin Aadenine Dinucleotide•2Na | 0.000106 |
| Folic Acid | 0.00001 |
| myo-Inositol | 0.00005 |
| 5-Methyldeoxycytidine | 0.0001 |
| β-NAD | 0.007 |
| β-NADP•Na | 0.001 |
| Niacinamide | 0.000025 |
| Nicotinic Acid | 0.000025 |
| D-Pantothenic Acid [hemicalcium] | 0.00001 |
| Pyridoxal•HCl | 0.000025 |
| Pyridoxine•HCl | 0.000025 |
| Riboflavin | 0.00001 |
| Thiamine•HCl | 0.00001 |
| Thymidine | 0.01 |
| Uridine-5-Triphosphate•Na | 0.001 |
| Calcium Chloride [Anhydrous] | 0.2 |
| Magnesium Sulfate [Anhydrous] | 0.09769 |
| Potassium Chloride | 0.4 |
| Sodium Acetate [Anhydrous] | 0.05 |
| Sodium Chloride | 6.8 |
| Sodium Phosphate Monobasic [Anhydrous] | 0.122 |
| D-Glucose | 1.0 |
| Phenol Red•Na | 0.02124 |
| Glutathione | 0.01 |
| D-Glucuronic Acid•Na | 0.00388 |
| Cholesterol | 0.0002 |
| Tween 80 | 0.005 |

TABLE 4

| A1ATD-iPSC line | Clones analyzed | Het.[a] | Homo./Hemi.[b] | Het. + additional integrations[c] | Homo./Hemi. + additional integrations[c] | Non-targeted[d] |
|---|---|---|---|---|---|---|
| A | 84 | 45 | 3 | 23 | 8 | 5 |
| B | 18 | 10 | 2 | 3 | 3 | 0 |
| C[e] | 216 | 112 | 9 | 52 | 21 | 22 |
| Mean frequency [%] | | 54 | 6 | 23 | 12 | 5 |

[a] Het., clones heterozygous for PB allele.

[b] Homo./Hemi., clones homozygous or hemizygous for PB allele. Cells with one targeted allele and deletion of the other allele are undistinguishable from correctly targeted homozygous clones by PCR. Such cells are designated as hemizygotes.

[c] Vector backbone integration was analyzed by PCR.

[d] Clones showing incorrect PCR bands are included.

[e] A sum of 2 independent experiments.

TABLE 5

| Cell line | Clones analyzed | Bi-allelic excision w/o re-integration | | Bi-allelic excision w/ re-integration | |
|---|---|---|---|---|---|
| | | No. of clones | Frequency [%] | No. of clones | Frequency [%] |
| B-16 | 88 | 15 | 17 | 33 | 38 |
| C-G4 | 94 | 5 | 5 | 19 | 20 |
| | | | Mean frequency [%] 11 | | 29 |

The invention claimed is:

1. A method for inducing hepatic differentiation comprising;
   (i) providing a population of mammalian induced pluripotent stem (iPS) cells,
   (ii) culturing the population in a endoderm induction medium,
   wherein the endoderm induction medium is a chemically defined medium which comprises fibroblast growth factor; a TGFβ ligand selected from activin and TGFβ; bone morphogenic protein; a phosphatidylinositol 3-kinase (PI3K) inhibitor; and a glycogen synthase kinase 3β (GSK3β) inhibitor,
   (iii) further culturing the population in step (ii) in a second endoderm induction medium, wherein the second endoderm induction medium is a chemically defined medium which comprises fibroblast growth factor; a TGFβ ligand selected from activin and TGFβ; bone morphogenic protein and a phosphatidylinositol 3-kinase (PI3K) inhibitor and lacks GSK3β inhibitor,
   (iv) further culturing the population in step (iii) in anterior definitive endoderm (ADE) induction medium which comprises a TGFβ ligand selected from activin and fibroblast growth factor to produce the population of anterior definitive endoderm (ADE) cells and,
   (v) culturing the population of ADE cells in a hepatic induction medium to produce a population of hepatic progenitor cells,
   wherein the hepatic induction medium is a chemically defined medium which consists of a chemically defined basal medium and a TGFβ ligand selected from activin and TGFβ.

2. The method of claim 1, wherein the TGFβ ligand is activin.

3. The method of claim 1, wherein the PI3K inhibitor is LY294002.

4. The method of claim 1, wherein the GSK3β inhibitor is CHIR99021.

5. The method of claim 1 further comprising;
   (vi) culturing the population of hepatic progenitor cells in a hepatic maturation medium to produce a population of hepatocytes.

6. The method of claim 1 further comprising expanding, culturing, maintaining or sorting the population of hepatic progenitor cells.

7. The method of claim 5 further comprising expanding, culturing, maintaining or sorting the population of hepatocytes.

8. The method of claim 5 further comprising admixing the population of hepatocytes with a pharmaceutically acceptable excipient.

9. The method of claim 1, wherein the iPS cells are human iPS cells.

10. The method of claim 5, wherein the iPS cells are derived from cells obtained from an individual with a liver disease and the hepatocytes in the population display a disease phenotype.

11. The method of claim 10, wherein the liver disease is an inherited metabolic disorder (IMD).

12. The method of claim 11, wherein the IMD is selected from the group consisting of Alpha 1 Antitrypsin deficiency, a Glycogen Storage Disease, Familial Hypercholesterolemia, Hereditary Tyrosinaemia, Crigler Najjar syndrome, ornithine transcarbamylase deficiency, factor IX deficiency, haemochromatosis, Wilson's disease, Dubin-Johnson syndrome, familial amyloidosis, and Refsum's disease.

* * * * *